(12) United States Patent
Pandey et al.

(10) Patent No.: US 7,943,640 B2
(45) Date of Patent: May 17, 2011

(54) COMPOSITIONS AND METHODS FOR INHIBITING TGF-β

(75) Inventors: Anjali Pandey, Fremont, CA (US); Robert M. Scarborough, Half Moon Bay, CA (US); Meenakshi S. Venkatraman, Foster City, CA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 572 days.

(21) Appl. No.: 11/941,284

(22) Filed: Nov. 16, 2007

(65) Prior Publication Data

US 2008/0108656 A1    May 8, 2008

Related U.S. Application Data

(63) Continuation of application No. 10/869,321, filed on Jun. 15, 2004, now Pat. No. 7,314,939.

(60) Provisional application No. 60/479,488, filed on Jun. 17, 2003.

(51) Int. Cl.
*A61K 31/04* (2006.01)
(52) U.S. Cl. ............... 514/312; 514/313; 514/314
(58) Field of Classification Search ............ 514/312, 514/313, 314
See application file for complete search history.

(56) References Cited

U.S. PATENT DOCUMENTS

| | | | |
|---|---|---|---|
| 4,739,762 A | 4/1988 | Palmaz | |
| 5,195,984 A | 3/1993 | Schatz | |
| 5,780,482 A | 7/1998 | Armitage et al. | |
| 6,277,989 B1 | 8/2001 | Chakravarty et al. | |
| 6,476,031 B1 | 11/2002 | Chakravarty et al. | |
| 6,638,945 B1 | 10/2003 | Gibson | |
| 6,809,106 B1 | 10/2004 | Gibson | |
| 2005/0009815 A1 | 1/2005 | DeVita et al. | |

FOREIGN PATENT DOCUMENTS

| | | |
|---|---|---|
| EP | 0 705 260 B1 | 3/1999 |
| WO | WO 00/12497 A1 | 3/2000 |
| WO | WO 02/079165 A1 | 10/2002 |

OTHER PUBLICATIONS

Shi, Cell, vol. 113, pp. 685-700, Jun. 13, 2003.*
Medicherla, CA 148:552951, abstract only of Anticancer Research, vol. 27(6B), pp. 4149-4157, 2007.*
Halder, CA 143:109228, abstract only of Neoplasia, vol. 7(5), pp. 509-521, 2005.*
Roberts and Sporn, "The Transforming Growth Factor-βs" in: *Peptide Growth Factors and Their Receptors. I. Handbook of Experimental Pharmacology*, Springer-Verlag, Berlin, 1990, vol. 95, No. 1, pp. 419-472.
Berge et al., "Pharmaceutical Salts," *J. of Pharmaceutical Science*, 1977, vol. 66, pp. 1-19.
Bundgaard, H. (Ed.) *Design of Prodrugs*, pp. 7-9 and 21-24, Elsevier, Amsterdam, 1985.
Derynck, R. et al., "Nomenclature: Vertebrate mediators of TGFβ Family Signals," *Cell*, 1996, vol. 87, p. 173.
Derynck R. and Y. Zhang, "Intracellular signaling: The Mad way to do it," *Curr. Biol.*, 1996, vol. 6, pp. 1226-1229.
Derynck, R., "TGF-β-receptor-mediated signaling," *Trends Biochem. Sci.*, 1994, vol. 19, pp. 548-553.
Dijke, P. et al., "Signaling via hetero-oligomeric complexes of type I and type II serine/threoine kinase receptors," *Curr. Opin. Cell Biol.*, 1996, vol. 8, pp. 139-145.
Eppert, K. et al., "MADR2 maps to 18q21 and encodes a TGFβ-regulated MAD-related protein that is functionally mutated in colorectal carcinoma," *Cell*, 1996, vol. 86, pp. 543-552.
Grainger, D.J. and J.C. Matcliffe, "A pivotal role for TGF-β in atherogenesis?" *Bio. Rev. Cambridge Phil. Soc.*, 1995, vol. 70, pp. 571-596.
Hahn, S.A. et al., "DPC4, a candidate tumor suppressor gene at human chromosome 18q21.1" *Science*, 1996, vol. 271, pp. 350-353.
Hoodless, P.A. et al., "MADR1, a MAD-related protein that functions in BMP2 Signaling Pathways," *Cell*, 1996, vol. 85, pp. 489-500.
Hoosein, N.M. et al., "Differential sensitivity of subclasses of human colon carcinoma cell lines to the growth inhibitory effects of transforming growth factor-β1," *Exp. Cell. Res.*, 1989, vol. 181, pp. 442-453.
Kretzschmar, M. et al., "The TGF-β family mediator Smad1 is phosphorylated directly and activated functionally by the BMP receptor kinase," *Genes Dev.*, 1997, vol. 11, pp. 984-995.
Lagna, G. et al., "Partnership between DPC4 and SMAD proteins in TGF-β signaling pathways," *Nature*, 1996, vol. 383, pp. 832-836.
Lin H.Y. and H.F. Lodish, "Receptors for the TGF-β superfamily: multiple polypeptides and serine/threonine kinases," *Trends Cell Biol.*, 1993, vol. 3, No. 1; pp. 14-19.
Liu, F. et al., "A human Mad protein acting as a BMP-regulated transcriptional activator," *Nature*, 1996, vol. 381, pp. 620-623.
Massagué, J. and F. Weis-Garcia, "Serine/threonine kinase receptors: Mediators of transforming growth factor beta family signals," *Cancer Surv.*, 1996, vol. 27, pp. 41-64.

(Continued)

*Primary Examiner* — D. Margaret Seaman
(74) *Attorney, Agent, or Firm* — Kilpatrick Townsend & Stockton LLP

(57) ABSTRACT

The present invention provides compounds of the formula:

and pharmaceutically acceptable isomers, salts, hydrates, solvates, and prodrug derivatives thereof, wherein $R^1$, $R^6$, $R^7$, $R^8$, Pg, and n are those defined herein. The present invention also provides pharmaceutical compositions comprising the same and methods for using the same. In particular, compounds of Formula I are useful in modulating TGF-β activity.

23 Claims, No Drawings

OTHER PUBLICATIONS

Massagué, J., "TGF-β signaling: Receptors, transducers, and Mad proteins," *Cell*, 1996, vol. 85, pp. 947-950.

Meersseman, G. et al., "The C-terminal domain of Mad-like signal transducers is sufficient for biological activity in the *Xenophus* embryo and transcriptional activation," *Mech. Dev.*, 1997, vol. 61, pp. 127-140.

Metcalfe, J. and D.J. Grainger, "TGF-β: Implications for human vascular disease," *J. Human Hypertens.*, 1995, vol. 9, pp. 679.

Murthy, U. et al., "Expression of TGF-α/EGF and TGF-β receptors in human colon carcinoma cell lines," *Int'l. J. Cancer*, 1989, vol. 44, pp. 110-115.

Nakao, A. et al., "Transient gene transfer and expression of Smad7 prevents bleomycin-induced lung fibrosis in mice," *J. Clin. Inv.*, 1999, vol. 104, pp. 5-11.

Newfeld, S.J. et al., "*Mothers against dpp* encodes a conserved cytoplasmic protein required in DPP/TGF-β responsive cells," *Development*, 1996, vol. 122, pp. 2099-2108.

Riggins, G. et al., "Mad-related genes in the human," *Nature Genet.*, 1996, vol. 13, pp. 347-349.

Sato, M. et al., "Transforming growth factor-$β_1$ proliferated vascular smooth muscle cells from spontaneously hypertensive rats," *Am. J. Hypertens.*, 1995, vol. 8, pp. 160-166.

Savage, C. et al., "*Caenorhabditis elegans* genes *sma-2, sma-3, and sma-4* define a conserved family of transforming growth factor β components," *Proc. Natl. Acad. Sci. USA*, 1996, vol. 93, pp. 790-794.

Schulick, A.H. et al., "Overexpression of transforming growth factor β1 in arterial endothelium causes hyperplasia, apoptosis, and cartilaginous metaplasia," *Proc. Natl. Acad. Sci. USA*, 1988, vol. 95, pp. 6983-6988.

Sekelsky, J.J. et al., "Genetic Characterization and cloning of *Mothers against dpp*, a gene required for *decapentaplegic* function in *Drosophila melanogaster*," *Genetics*, 1995, vol. 139, pp. 1347-1358.

Shull, M.M. et al., "Targeted disruption of the mouse transforming growth factor-β1 gene results in multifocal inflammatory disease," *Nature*, 1992, vol. 359, pp. 693-699.

Silverman, R.B., *The Organic Chemistry of Drug Design and Drug Action*, pp. 352-401, Academic Press, San Diego, CA, 1992.

Wahl, S.M. et al., "Inflammatory and immunomodulatory roles of TGF-β," *Immunol. Today*, 1989, vol. 10, pp. 258-261.

Welch, D.R. et al., Transforming growth factor β stimulates mammary adenocarcinoma cell invasion and metastatic potential, *Proc. Natl. Acad. Sci. USA*, 1990, vol. 87, pp. 7678-7682.

Wiersdorf, V. et al., "Mad acts downstream of Dpp receptors, revealing a differential requirement for *dpp* signaling in initiation and propagation of morphogenesis in the *Drosophila* eye," *Development*, 1996, vol. 122, pp. 2153-2163.

Wieser, R. et al., "GS domain mutations that constitutively activate TβR-I, the downstream signaling component in the TGF-β receptor complex," *EMBO J.*, 1995, 14, pp. 2199-2208.

Wrana, J.L. et al., "Mechanism of activation of the TGF-β receptor," *Nature*, 1994, vol. 370, pp. 341-347.

Wrana, J.L. and L. Attisano, "MAD-related proteins in TGF-β signaling," *Trends Genet.*, 1996, vol. 12, pp. 493-496.

Wu, R.Y. et al., "Heteromeric and homomeric interactions correlate with signaling activity and functional cooperativity of Smad3 and Smad4/DPC4," *Mol. Cell. Biol.*, 1997, vol. 17, pp. 2521-2528.

Ziyadeh, F.N. et al., "Long-term prevention of renal insufficiency, excess matrix gene expression, and glomerular mesangial matrix expansion by treatment with monoclonal antitransforming growth factor-β antibody in *db/db* diabetic mice," *Proc. Natl. Acad. Sci.*, 2000, vol. 97, pp. 8015-8020.

Berge et al., "Pharmaceutical Salts," *J. of Pharmaceutical Science*, 1977, vol. 66, pp. 1-19.

Bundgaard, H. (Ed.) *Design of Prodrugs*, pp. 7-9 and 21-24, Elsevier, Amsterdam, 1985.

Derynck R. and Y. Zhang, "Intracellular signaling: The Mad way to do it," *Curr. Biol.*, 1996, vol. 6, pp. 1226-1229.

Derynck, R. et al., "Nomenclature: Vertebrate mediators of TGFβ Family Signals," *Cell*, 1996, vol. 87, p. 173.

Derynck, R., "TGF-β-receptor-mediated signaling," *Trends Biochem. Sci.*, 1994, vol. 19, pp. 548-553.

Dijke, P. et al., "Signaling via hetero-oligomeric complexes of type I and type II serine/theroine kinase receptors," *Curr. Opin. Cell Biol.*, 1996, vol. 8, pp. 139-145.

Eppert, K. et al., "MADR2 maps to 18q21 and encodes a TGFβ-regulated MAD-related protein that is functionally mutated in colorectal carcinoma," *Cell*, 1996, vol. 86, pp. 543-552.

Grainger, D.J. and J.C. Matcliffe, "A pivotal role for TGF-β in atherogenesis?" *Bio. Rev. Cambridge Phil. Soc.*, 1995, vol. 70, pp. 571-596.

Hahn, S.A. et al., "DPC4, a candidate tumor suppressor gene at human chromosome 18q21.1" *Science*, 1996, vol. 271, pp. 350-353.

Hoodless, P.A. et al., "MADR1, a MAD-related protein that functions in BMP2 Signaling Pathways," *Cell*, 1996, vol. 85, pp. 489-500.

Hoosein, N.M. et al., "Differential sensitivity of subclasses of human colon carcinoma cell lines to the growth inhibitory effects of transforming growth factor-β1," *Exp. Cell. Res.*, 1989, vol. 181, pp. 442-453.

Kretzschmar, M. et al., "The TGF-β family mediator Smad1 is phosphorylated directly and activated functionally by the BMP receptor kinase," *Genes Dev.*, 1997, vol. 11, pp. 984-995.

Lagna, G. et al., "Partnership between DPC4 and SMAD proteins in TGF-β signaling pathways," *Nature*, 1996, vol. 383, pp. 832-836.

Lin H.Y. and H.F. Lodish, "Receptors for the TGF-β superfamily: multiple polypeptides and serine/threonine kinases," *Trends Cell Biol.*, 1993, vol. 3, No. 1; pp. 14-19.

Liu, F. et al., "A human Mad protein acting as a BMP-regulated transcriptional activator," *Nature*, 1996, vol. 381, pp. 620-623.

Massagué, J. and F. Weis-Garcia, "Serine/theronine kinase receptors: Mediators of transforming growth factor beta family signals," *Cancer Surv.*, 1996, vol. 27, pp. 41-64.

Massagué, J., "TGF-β signaling: Receptors, transducers, and Mad proteins," *Cell*, 1996, vol. 85, pp. 947-950.

Meersseman, G. et al., "The C-terminal domain of Mad-like signal transducers is sufficient for biological activity in the *Xenophus* embryo and transcriptional activation," *Mech. Dev.*, 1997, vol. 61, pp. 127-140.

Metcalfe, J. and D.J. Grainger, "TGF-β: Implications for human vascular disease," *J. Human Hypertens.*, 1995, vol. 9, pp. 679.

Murthy, U. et al., "Expression of TGF-α/EGF and TGF-β receptors in human colon carcinoma cell lines," *Int'l J. Cancer*, 1989, vol. 44, pp. 110-115.

Nakao, A. et al., "Transient gene transfer and expression of Smad7 prevents bleomycin-induced induced lung fibrosis in mice," *J. Clin. Inv.*, 1999, vol. 104, pp. 5-11.

Newfeld, S.J. et al., "*Mothers against dpp* encodes a conserved cytoplasmic protein required in DPP/TGF-β responsive cells," *Development*, 1996, vol. 122, pp. 2099-2108.

Riggins, G. et al., "Mad-related genes in the human," *Nature Genet.*, 1996, vol. 13, pp. 347-349.

Roberts and Sporn, "The Transforming Growth Factor-βs" in: *Peptide Growth Factors and Their Receptors. I. Handbook of Experimental Pharmacology*, Springer-Verlag, Berlin, 1990, vol. 95. No. 1, pp. 419-472.

Sato, M. et al., "Transforming growth factor-$β_1$ proliferated vascular smooth muscle cells from spontaneously hypertensive rats," *Am. J. Hypertens.*, 1995, vol. 8, pp. 160-166.

Savage, C. et al., "*Caenorhabditis elegans* genes *sma-2, sma-3, and sma-4* define a conserved family of transforming growth factor β components," *Proc. Natl. Acad. Sci. USA*, 1996, vol. 93, pp. 790-794.

Schulick, A.H. et al., "Overexpression of transforming growth factor β1 in arterial endothelium causes hyperplasia, apoptosis, and cartilaginous metaplasia," *Proc. Natl. Acad. Sci. USA*, 1988, vol. 95, pp. 6983-6988.

Sekelsky, J.J. et al., "Genetic characterization and cloning of *Mothers against dpp*, a gene required for *decapentaplegic* function in *Drosophila melanogaster*," *Genetics*, 1995, vol. 139, pp. 1347-1358.

Shull, M.M. et al., "Targeted disruption of the mouse transforming growth factor-β1 gene results in multifocal inflammatory disease," *Nature*, 1992, vol. 359, pp. 693-699.

Silverman, R.B., *The Organic Chemistry of Drug Design and Drug Action*, pp. 352-401, Academic Press, San Diego, CA, 1992.

Wahl, S.M. et al., "Inflammatory and immunomodulatory roles of TGF-β," *Immunol. Today*, 1989, vol. 10, pp. 258-261.

Welch, D.R. et al., Transforming growth factor β stimulates mammary adenocarcinoma cell invasion and metastatic potential, *Proc. Natl. Acad. Sci. USA.*, 1990, vol. 87, pp. 7678-7682.

Wiersdorf, V. et al., "Mad acts downstream of Dpp receptors, revealing a differential requirement for *dpp* signaling in initiation and propagation of morphogenesis in the *Drosophila* eye," *Development*, 1996, vol. 122, pp. 2153-2163.

Wieser, R. et al., "GS domain mutations that constitutively activate TβR-I, the downstream signaling component in the TGF-β receptor complex," *EMBO J.*, 1995, 14, pp. 2199-2208.

Wrana, J.L. and L. Attisano, "MAD-related proteins in TGF-β signaling," *Trends Genet.*, 1996, vol. 12, pp. 493-496.

Wrana, J.L. et al., "Mechanism of activation of the TGF-β receptor," *Nature*, 1994, vol. 370, pp. 341-347.

Wu, R.Y. et al., "Heteromeric and homomeric interactions correlate with signaling activity and functional cooperativity of Smad3 and Smad4/DPC4," *Mol. Cell. Biol.*, 1997, vol. 17, pp. 2521-2528.

Ziyadeh, F.N. et al., "Long-term prevention of renal insufficiency, excess matrix gene expression, and glomerular mesangial matrix expansion by treatment with monoclonal antitransforming growth factor-β antibody in *db/db* diabetic mice," *Proc. Natl. Acad. Sci.*, 2000, vol. 97, pp. 8015-8020.

Blobe et al. *N. Engl. J. Med.* May 4, 2000; 342(18):1350-8.

\* cited by examiner

COMPOSITIONS AND METHODS FOR INHIBITING TGF-β

CROSSED-REFERENCE TO RELATED APPLICATION

This application is a continuation of U.S. patent application Ser. No. 10/869,321, filed Jun. 15, 2004 now U.S. Pat. No. 7,314,939 which claims the benefit of U.S. Provisional Patent Application No. 60/479,488, filed Jun. 17, 2003, the content of which is incorporated herein by reference.

FIELD OF THE INVENTION

This invention relates to compounds that are useful in modulating the transforming growth factor (TGF)-β signaling pathway.

BACKGROUND OF THE INVENTION

TGF-β belongs to a large super-family of multifunctional polypeptide factors. The TGF-β family includes three genes, TGF-β1, TGF-β2 and TGF-β3, which are pleiotropic modulators of cell growth and differentiation, embryonic and bone development, extracellular matrix formation, hematopoiesis, immune and inflammatory responses. For example, TGF-β1 inhibits the growth of many cell types, including epithelial cells, but stimulates the proliferation of various types of mesenchymal cells.

The TGF-β genes have high homology with one another. In mammals, the TGF-β super-family includes various TGF-β genes, as well as the embryonic morphogenes, such as the family of the activins, inhibins, "Mullerian Inhibiting Substance", and bone morphogenic protein (BMP). See Roberts and Sporn, "The Transforming Growth Factor-βs in Peptide Growth Factors and Their Receptors. I." *Handbook of Experimental Pharmacology*, vol. 95/I, Springer-Verlag, Berlin, 1990, pp 419-472. Each member of the TGF-β family exerts a wide range of biological effects on a large variety of cell types, e.g., they regulate cell growth, morphogenesis, differentiation, matrix production and apoptosis. Lagna et al., *Nature*, 1996, 383, 832-836. TGF-β acts as a growth inhibitor for many cell types and is believed to play a central role in the regulation of embryonic development, tissue regeneration, immuno-regulation, as well as in fibrosis and carcinogenesis.

In addition, TGF-β induces the synthesis of extracellular matrix (ECM) proteins, modulates the expression of matrix proteinases and proteinase inhibitors and changes the expression of integrins. ECM is a dynamic superstructure of self aggregating macromolecules including fibronectin, collagen and proteoglycan. It is believed that ECM is the chief pathologic feature of fibrotic diseases. ECM disorder has also been proposed to the chief pathologic feature of fibrotic diseases. ECM disorder has also been proposed to play a central role in pathogenesis disorders such as hypertensive vascular disease and diabetic renal disease. Sato et al., *Am. J. Hypertens.*, 1995, 8, 160-166 (1995); Schulick et al., *Proc. Natl. Acad. Sci.*, 1988, 95, 6983-6988. Moreover, TGF-β is expressed in large amounts in many tumors. Derynck, *Trends Biochem. Sci.*, 1994, 19, 548-553. This strong occurrence in neoplastic tissues could indicate that TGF-β is strategic growth/morphogenesis factor which influences the malignant properties associated with the various stages of the metastatic cascade. TGF-β inhibits the growth of normal epithelial and relatively differentiated carcinoma cells, whereas undifferentiated tumor cells which lack many epithelial properties are generally resistant to growth inhibition by TGF-β. Hoosein et al., *Exp. Cell. Res.*, 1989, 181, 442-453; Murthy et al., *Init'l. J. Cancer*, 1989, 44, 110-115. Furthermore, TGF-β1 is believed to potentiate the invasive and metastatic potential of a breast adenoma cell line (Welch et al., *Proc. Natl. Acad. Sci.*, 1990, 87, 7678-7682), which indicates a role of TGF-β1 in tumor progression.

The cellular effects of TGF-β are exerted by ligand-induced hetero-oligomerization of two distantly related type I and type II serine/threonine kinase receptors, TGF-βR-I and TGF-βR-II, respectively. Lin et al., *Trends Cell Biol.*, 1993, 11, 972-978; Massague et al., *Cancer Surv.*, 1996, 27, 41-64; Dijke et al., *Curr. Opin. Cell Biol.*, 1996, 8, 139-145. The two receptors, both of which are required for signaling, act in sequence: TGF βR-I is a substrate for the constitutively active TGF-βR-II kinase. Wrana et al., *Nature*, 1994, 370, 341-347; Wieser et al., *EMBO J.*, 1995, 14, 2199-2208. Upon TGF-β1 binding, the type II receptor phosphorylates threonine residues in GS domain of ligand occupied type I receptor or activin like kinase (ALK5), which results in activation of type I receptors. The TGF-β1 type I receptor in turn phosphorylates Smad2 and Smad3 proteins which translocate to the nucleus and mediate intracellular signaling. The inhibition of ALK5 phosphorylation of Smad3 reduces TGF-β1 induced extracellular matrix production. Krettzchmar et al., *Genes Dev.*, 1997, 11, 984-995; Wu et al., *Mol. Cell. Biol.*, 1997, 17, 2521-2528.

TGF-β is also a powerful and essential immune regulator in the vascular system capable of modulating inflammatory events in both leuko and vascular endothelial cells. Shull et al., *Nature*, 1992, 359, 693-699. It is also involved in the pathogenesis of chronic vascular diseases such as atherosclerosis and hypertension. Grainger & Metcalfe et al., *Bio. Rev. Cambridge Phil. Soc.*, 1995, 70, 571-596; Metcalfe et al., *J. Human Hypertens.*, 1995, 9, 679.

Genetic studies of TGF-β-like signaling pathways in *Drosophila* and *Caenorhabditis elegans* have led to the identification of mothers against dpp (Mad) and sma genes, respectively. Sekelsky et al., *Genetics*, 1995, 139, 1347-1358; Savage et al., *Proc. Natl. Acad. Sci. USA*, 1996, 93, 790-794. The products of these related genes perform essential functions downstream of TGF-β like ligands acting via serine/threonine kinase receptors in these organisms. Wiersdorf et al., *Development*, 1996, 122, 2153-2163; Newfeld et al., *Development*, 1996, 122, 2099-2108; Hoodless et al., *Cell*, 1996, 85, 489-500.

Vertebrate homologs of Mad and sma have been termed Smads or MADR genes. Derynck et al., *Cell*, 1996, 87, 173; Wrana et al., *Trends Genet.*, 1996, 12, 493-496. Smad proteins have been identified as signaling mediators of TGF-β super family. Hahn et al., *Science*, 1996, 271, 350-353. Genetic alterations in Smad2 and Smad4/DPC4 have been found in specific tumor subsets, and thus Smads may function as tumor suppressor genes. Hahn et al., *Science*, 1996, 271, 350-353; Riggins et al., *Nature Genet.*, 1996, 13, 347-349; Eppert et al., *Cell*, 1996, 86, 543-552. Smad proteins share two regions of high similarity, termed MH1 and MH2 domains, connected with a variable proline-rich sequence. Massague, *Cell*, 1996, 85, 947-950; Derynck et al., *Curr. Biol.*, 1996, 6, 1226-1229. The C-terminal part of Smad2, when fused to a heterologous DNA-binding domain, was found to have transcriptional activity. Liu et al., *Nature*, 1996, 381, 620-623; Meersseman et al., *Mech. Dev.*, 1997, 61, 127-140. The intact Smad2 protein when fused to a DNA-binding domain, was latent, but transcriptional activity was unmasked after stimulation with ligand. Liu et al., supra.

TGF-β initiates an intracellular signaling pathway leading ultimately to the expression of genes that regulate the cell cycle, control proliferative responses, or relate to extracellular matrix proteins that mediate outside-in cell signaling, cell adhesion, migration and intercellular communication.

TGF-β is also an important mediator of diabetic nephtopathy, a common complication in patients with either type 1 or type 2 diabetes mellitus. Ziyadeh et al., *Proc. Natl. Acad. Sci.*, 2000, 97, 8015-8020 evaluated the role of renal TGF-β in the development of chronic structural and functional changes of diabetic nephropathy by assessing the response of db/db mice to chronic treatment with neutralizing anti-TGF-β1 and generalized (tubular and glomerular) up-regulation of TGF-βtype II receptor. The antibody effectively prevented increases in renal expression of matrix genes including type IV collagen and fibronectin and may have also stimulated matrix degradative pathways because TGF-β suppresses the activity of metalloproteinases and increase the expression of protease inhibitors such as plasminogen activator inhibitor-1 (PAI-1).

There exists a need for effective therapeutic agents for inhibiting TGF-β activity, as well as for inhibiting the phosphorylation of smad2 or smad3 by TGF-β type I or activin like kinase (ALK5) receptor and for preventing and treating disease states mediated by the TGF-β signaling pathway in mammals. In particular, there continues to be a need for compounds which selectively inhibit TGF-β.

SUMMARY OF THE INVENTION

The present invention provides compounds of the formula:

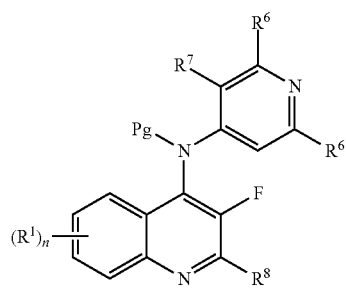

I or a pharmaceutically acceptable salt or a prodrug thereof, wherein

Pg is hydrogen, alkyl, or a nitrogen protecting group;
n is an integer from 0 to 3;
each $R^1$ substituent is independently selected from the group consisting of —$R^2$, -T-$R^2$, and —V-T-$R^2$;
wherein
each $R^2$ is independently selected from the group consisting of $C_{1-3}$ aliphatic, hydroxy, —N($R^3$)$_2$, halo, cyano, —O$R^4$, —C(O)$R^4$, —CO$_2R^4$, —S$R^4$, —S(O)$R^4$, —S(O)$_2R^4$, —N($R^3$)C(O)$R^4$, —N($R^3$)CO$_2R^4$, —N($R^3$)SO$_2R^4$, —C(O)N($R^3$)$_2$, —SO$_2$N($R^3$)$_2$, —N($R^3$)C(O)N($R^3$)$_2$, —OC(O)$R^4$, phenyl which is optionally substituted with 1-3 $R^5$, 5-6 membered heterocyclyl which is optionally substituted with 1-3 $R^5$, and 5-6 membered heteroaryl which is optionally substituted with 1-3 $R^5$;
each T is independently $C_{1-5}$ alkylidene that is optionally interrupted by —O—, —C(O)—, —S—, —S(O)—, —S(O)$_2$—, or —N($R^3$)—;
each V is independently selected from the group consisting of —O—, —S—, —S(O)—, —S(O)$_2$—, —C(O)—, —N($R^3$)—, —N($R^3$)C(O)—, or —N($R^3$)C(O)$_2$—, —N($R^3$)S(O)$_2$—, —C(O)N($R^3$)—, —S(O)$_2$N($R^3$)—, —N($R^3$)C(O)N($R^3$)—, and —OC(O)—;
each $R^3$ is independently selected from the group consisting of hydrogen, $C_{1-6}$ aliphatic, —C(O)$R^4$, —C(O)$_2R^4$, and —SO$_2R^4$,
or two $R^3$ on the same nitrogen together with their intervening nitrogen form a 5-6 membered heterocyclyl or heteroaryl ring having 1-3 ring heteroatoms selected from nitrogen, oxygen or sulfur;
each $R^4$ is independently selected from the group consisting of $C_{1-6}$ aliphatic, phenyl or a 5-6 membered heteroaryl or heterocyclyl having 1-3 ring heteroatoms selected from nitrogen, oxygen or sulfur;
$R^8$ is selected from the group consisting of:
(a) aryl, heteroaryl, and cycloalkyl, each of which is optionally substituted with 1-3 $R^5$, and
(b) alkyl;
wherein
each $R^5$ is independently selected from the group consisting of $C_{1-6}$ aliphatic, halo, —OH, —N($R^3$)$_2$, cyano, —O$R^4$, —C(O)$R^4$, —CO$_2R^4$, —S$R^4$, —S(O)$R^4$, —S(O)$_2R^4$, —N($R^3$)C(O)$R^4$, —N($R^3$)CO$_2R^4$, —N($R^3$)$_5$SO$_2R^4$, —C(O)N($R^3$)$_2$, —SO$_2$N($R^3$)$_2$, —N($R^3$)C(O)N($R^3$)$_2$, —OC(O)$R^4$, —OC(O)N($R^3$)$_2$, phenyl, 5-6 membered heterocyclyl and 5-6 membered heteroaryl,
or two adjacent $R^5$ on an aryl, cycloalkyl, or heteroaryl ring are taken together with their intervening atoms to form a 5-6 membered fused ring having 0-2 heteroatoms selected from nitrogen, oxygen or sulfur;
each $R^6$ is independently selected from the group consisting of hydrogen, halo, $C_{1-4}$ alkyl, $C_{1-4}$ alkoxy, $C_{1-4}$ monoalkylamino and $C_{1-4}$ dialkylamino; and
$R^7$ is selected from the group consisting of hydrogen, halo, —OH, —N($R^3$)$_2$, cyano, —O$R^4$, —C(O)$R^4$, —CO$_2R^4$, —S$R^4$, —S(O)$R^4$, —S(O)$_2R^4$—N($R^3$)C(O)$R^4$—N($R^3$)CO$_2R^4$, —N($R^3$)SO$_2R^4$, —C(O)N($R^3$)$_2$, —SO$_2$N($R^3$)$_2$, —N($R^3$)C(O)N($R^3$)$_2$, and —OC(O)$R^4$.

Compounds of Formula I, and compositions comprising the same, are useful in a variety of pharmaceutical applications. In particular, compounds of Formula I are useful in modulating TGF-β.

DETAILED DESCRIPTION OF THE INVENTION

Definitions

In accordance with the present invention and as used herein, the following terms are defined with the following meanings, unless stated otherwise.

"Alkyl" refers to a linear or branched saturated monovalent hydrocarbon moiety having from one to twelve, preferably one to nine and more preferably one to six, carbon atoms. Exemplary alkyl groups include methyl, ethyl, n-propyl, 2-propyl, tert-butyl, pentyl, and the like.

The term "aliphatic" as used herein means straight-chain, branched or cyclic $C_1$-$C_{12}$ hydrocarbons which are completely saturated or which contain one or more units of unsaturation but which are not aromatic. For example, suitable aliphatic groups include substituted or unsubstituted linear, branched or cycloalkyl, alkenyl, alkynyl groups and hybrids thereof such as (cycloalkyl)alkyl, (cycloalkenyl)alkyl or (cycloalkyl)alkenyl. Preferred aliphatic groups are optionally substituted linear or branched alkyl, alkenyl, and alkynyl groups, with the alkyl group being a particularly preferred aliphatic group.

An aliphatic group or a heterocyclic ring may contain one or more substituents. Examples of suitable substituents on the saturated carbon of an aliphatic group or of a heterocyclic ring include those listed herein for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group and a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

"Alkylidene" refers to an optionally substituted, straight or branched divalent carbon chain that may be fully saturated or have one or more units of unsaturation, e.g., alkylene, alkenylene, and alkynylene. The optional substituents are as described herein for an aliphatic group. Preferred alkylidene group is alkylene.

"Alkoxy" refers to a moiety of the formula —OR$^a$, wherein R$^a$ is alkyl as defined herein.

"Alkenyl" refers to a monovalent straight or branched chain containing two to twelve carbon atoms having one or more carbon-carbon double bonds.

"Alkynyl" refers to a monovalent straight or branched chain containing two to twelve carbon atoms having one or more carbon-carbon triple bonds.

The term "cycloalkyl, used alone or as part of a larger moiety, includes mono- or bicyclic $C_3$-$C_{12}$ hydrocarbons which are completely saturated or which contain one or more units of unsaturation, but which are not aromatic. Exemplary cycloalkyl groups include, cyclopropyl, cyclopentyl, cyclohexyl, and the like.

"Aryl" refers to a monovalent mono-, bi- or tri-cyclic aromatic hydrocarbon moiety having from 6 to 14 carbon ring atoms. Exemplary aryl groups include, but are not limited to, phenyl, 1-naphthyl, 2-naphthyl, anthracyl, and the like. Aryl group can be optionally substituted. Aryl also includes a group in which an aromatic ring is fused to one or more non-aromatic rings, such as in an indanyl, phenanthridinyl, or tetrahydronaphthyl, where the radical or point of attachment is on the aromatic ring.

Terms "halo", "halide" and "halogen" are used interchangeably herein and refer to fluoro, chloro, bromo, or iodo.

The terms "haloalkyl", "haloalkenyl" and "haloalkoxy", mean alkyl, alkenyl or alkoxy, as the case may be, substituted with one or more halogen atoms.

An aryl or heteroaryl group may contain one or more substituents. Examples of suitable substituents on the unsaturated carbon atom of an aryl and heteroaryl groups include a halogen, —R$^o$, —OR$^o$, —SR$^o$, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R$^o$)$_2$, —NR$^o$C(O)R$^o$, —NR$^o$C(O)N(R$^o$)$_2$, —NR$^o$CO$_2$R$^o$, —NR$^o$NR$^o$C(O)R$^o$, —NR$^o$NR$^o$C(O)N(R$^o$)$_2$, —NR$^o$NR$^o$CO$_2$R$^o$, —C(O)C(O)R$^o$, —C(O)CH$_2$C(O)R$^o$, —CO$_2$R$^o$, —C(O)R$^o$, —C(O)N(R$^o$)$_2$, —OC(O)N(R$^o$)$_2$, —S(O)$_2$R$^o$, —SO$_2$N(R$^o$)$_2$, —S(O)R$^o$, —NR$^o$SO$_2$N(R$^o$)$_2$, —NR$^o$SO$_2$R$^o$, —C(=S)N(R$^o$)$_2$, —C(=NH)—N(R$^o$)$_2$, —(CH$_2$)$_y$NHC(O)R$^o$, —(CH$_2$)$_y$NHC(O)CH(V—R$^o$)(R$^o$); wherein each R$^o$ is independently selected from hydrogen, a substituted or unsubstituted aliphatic group, an unsubstituted heteroaryl and heterocyclic ring, phenyl (Ph), substituted Ph, —O(Ph), substituted —O(Ph), —CH$_2$(Ph), and substituted —CH$_2$(Ph); wherein y is 0-6; and V is a linker group. Examples of substituents on the aliphatic group or the phenyl ring of R$^o$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated $C_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_4$—, —NH—, —SO$_2$NH—, or —NHSO$_2$—.

"Haloalkyl" refers to an alkyl group as defined herein that is substituted with one or more same or different halo atoms, e.g., —CH$_2$Cl, —CF$_3$, —CH$_2$CF$_3$, —CH$_2$CCl$_3$, and the like. The term "haloalkyl" also includes those alkyl groups in which all alkyl hydrogen atoms are replaced by halogen atoms, such as perfluoroalkyl groups.

"Heteroaryl" refers to a monovalent mono-, bi- or tri-cyclic aromatic moiety of five to twenty, preferably five to fourteen, ring atoms containing one to four, preferably one to three, hetero ring atoms each of which is independently selected from the group N, O, and S(O)$_z$ (wherein the subscript z is 0, 1 or 2), the remaining ring atoms being C. Exemplary heteroaryl groups include, but are not limited to, 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, benzoisoxazolyl, and the like. Heteroaryl also includes a group in which a heteroatomic ring is fused to one or more aromatic or nonaromatic rings where the point of attachment is on the heteroaromatic ring. Examples include tetrahydroquinolinyl, tetrahydroisoquinolinyl, and pyrido[3,4-d]pyrimidinyl. Heteroaryl can be optionally substituted.

"Heterocyclyl" refers to a non-aromatic mono-, bi- or tri-cyclic moiety having three to twenty, preferably five to fourteen, ring atoms in which one to four, preferably one to three, and more preferably one or two, ring atoms are heteroatoms each of which is independently selected from N, O, and S(O)$_z$ (wherein the subscript z is 0, 1 or 2), the remaining ring atoms being C, with the understanding that the number of hetero ring atoms is less than the total number of ring atoms present in the heterocyclyl moiety. Exemplary heterocyclyl groups include, but are not limited to, piperidinyl, piperazinyl, morpholino, pyrrolidinyl, 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl,

[1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. Heterocyclyl can also be optionally substituted.

"Pharmaceutically acceptable excipient (or carrier)" means an excipient that is useful in preparing a pharmaceutical composition that is generally safe. Suitable pharmaceutically acceptable excipients are well known to one skilled in the art and include excipients that are acceptable for veterinary or human pharmaceutical use.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are typically prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group (e.g., protecting group) that may be cleaved in vivo to regenerate the free hydroxyl, amino, or sulfhydryl group, respectively. Examples of prodrugs include, but are not limited to, esters (e.g., acetate, formate, and benzoate derivatives) and carbamates (e.g., N,N-dimethylaminocarbonyl) of hydroxy functional groups, and amides, carbamates and urea derivatives of amino functional groups, and the like. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992, all of which are incorporated herein by reference in their entirety). Moreover, the prodrug derivatives of the invention may be combined with other features known to one skilled in the art to enhance bioavailability.

As used herein, the terms "treating", "contacting" and "reacting", when referring to a chemical reaction, are used interchangeably herein and refer to adding or mixing two or more reagents under appropriate conditions to produce the indicated and/or the desired product. It should be appreciated that the reaction which produces the indicated and/or the desired product may not necessarily result directly from the combination of two or more reagents which were initially added, i.e., there may be one or more intermediates which are produced in the mixture which ultimately leads to the formation of the indicated and/or the desired product.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a subject or patient for treating a disease, is sufficient to effect such treatment for the disease. The "therapeutically effective amount" will vary depending on a variety of the factors, such as a particular compound used, the disease and its severity, the age, weight, and other factors of the subject to be treated.

As used herein, the terms "as defined herein" and "as defined above" when referring to a variable incorporates by reference the broad definition of the variable as well as preferred, more preferred and most preferred definitions, if any.

"Biological property" for the purposes herein means an in vivo effector or activity that is directly or indirectly performed by a compound that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen atom by a deuterium or tritium, or the replacement of a carbon by $^{13}C$ or $^{14}C$ are within the scope of this invention.

Compounds of the Present Invention

In one aspect, the present invention provides compounds of the formula:

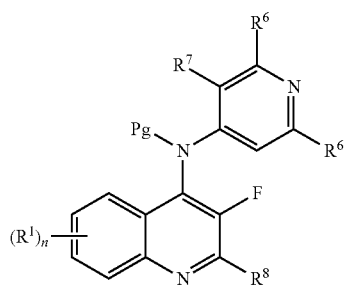

I wherein
Pg is hydrogen, alkyl, or a nitrogen protecting group;
n is an integer from 0 to 3;
each $R^1$ substituent is independently selected from the group consisting of —$R^2$, -T-$R^2$, and —V-T-$R^2$;
wherein
each $R^2$ is independently selected from the group consisting of $C_{1-3}$ aliphatic, hydroxy, —N($R^3$)$_2$, halo, cyano, —O$R^4$, —C(O)$R^4$, —CO$_2R^4$, —S$R^4$, —S(O)$R^4$, —S(O)$_2R^4$, —N($R^3$)C(O)$R^4$, —N($R^3$)CO$_2R^4$, —N($R^3$)SO$_2R^4$, —C(O)N($R^3$)$_2$, —SO$_2$N($R^3$)$_2$, —N($R^3$)C(O)N($R^3$)$_2$, —OC(O)$R^4$, phenyl which is optionally substituted with 1-3 $R^5$, 5-6 membered heterocyclyl which is optionally substituted with 1-3 $R^5$, and 5-6 membered heteroaryl which is optionally substituted with 1-3 $R^5$;
each T is independently $C_{1-5}$ alkylidene that is optionally interrupted by —O—, —C(O)—, —S—, —S(O)—, —S(O)$_2$—, or —N($R^3$)—;
each V is independently selected from the group consisting of —O—, —S—, —S(O)—, —S(O)$_2$—, —C(O)—, —N($R^3$)—, —N($R^3$)C(O)—, or —N($R^3$)C(O)$_2$—, —N($R^3$)S(O)$_2$—, —C(O)N($R^3$)—, —S(O)$_2$N($R^3$)—, —N($R^3$)C(O)N($R^3$)—, and —OC(O)—;
each $R^3$ is independently selected from the group consisting of hydrogen, $C_{1-6}$ aliphatic, —C(O)$R^4$, —C(O)$_2R^4$, and —SO$_2R^4$, or two $R^3$ on the same nitrogen together with their intervening nitrogen form a 5-6 membered heterocyclyl or heteroaryl ring having 1-3 ring heteroatoms selected from nitrogen, oxygen or sulfur;
each $R^4$ is independently selected from the group consisting of $C_{1-6}$ aliphatic, phenyl or a 5-6 membered heteroaryl or heterocyclyl having 1-3 ring heteroatoms selected from nitrogen, oxygen or sulfur;
$R^8$ is selected from the group consisting of:
(a) aryl, heteroaryl, and cycloalkyl, each of which is optionally substituted with 1-3 $R^5$, and
(b) alkyl;
wherein
each $R^5$ is independently selected from the group consisting of $C_{1-6}$ aliphatic, halo, —OH, —N($R^3$)$_2$, cyano, —O$R^4$, —C(O)$R^4$, —CO$_2R^4$, —S$R^4$, —S(O)$R^4$, —S(O)$_2R^4$, —N($R^3$)C(O)$R^4$, —N($R^3$)CO$_2R^4$, —N($R^3$)SO$_2R^4$, —C(O)N($R^3$)$_2$, —SO$_2$N($R^3$)$_2$, —N($R^3$)C(O)N($R^3$)$_2$, —OC(O)$R^4$, —OC(O)N($R^3$)$_2$, phenyl, 5-6 membered heterocyclyl and 5-6 membered heteroaryl,
or two adjacent $R^5$ on an aryl, cycloalkyl, or heteroaryl ring are taken together with their intervening atoms to form a 5-6 membered fused ring having 0-2 heteroatoms selected from nitrogen, oxygen or sulfur;
each $R^6$ is independently selected from the group consisting of hydrogen, halo, $C_{1-4}$ alkyl, $C_{1-4}$ alkoxy, $C_{1-4}$ monoalkylamino and $C_{1-4}$ dialkylamino; and
$R^7$ is selected from the group consisting of hydrogen, halo, —OH, —N($R^3$)$_2$, cyano, —O$R^4$, —C(O)$R^4$, —CO$_2R^4$, —S$R^4$, —S(O)$R^4$, —S(O)$_2R^4$, —N($R^3$)C(O)$R^4$, —N($R^3$)CO$_2R^4$, —N($R^3$)SO$_2R^4$, —C(O)N($R^3$)$_2$, —SO$_2$N($R^3$)$_2$, —N($R^3$)C(O)N($R^3$)$_2$, and —OC(O)$R^4$.

The compounds of the present invention can exist in unsolvated forms as well as solvated forms, including hydrated forms, all of which are intended to be encompassed within the scope of the invention. The scope of the present invention also includes all pharmaceutically acceptable salts, prodrugs and isomers, particularly stereoisomers, of compounds of Formula I. Unless otherwise stated, the term "stereoisomer" includes a pure chiral form, a racemic mixture and an enantiomerically and/or diastereomerically enriched forms. Furthermore, some compounds of the present invention can exist in tautomeric forms which are also intended to be encompassed within the scope of the present invention.

Some compounds of Formula I are capable of forming pharmaceutically acceptable salts. As stated above, these salts are also contemplated to be within the scope of the present invention. Pharmaceutically acceptable acid addition salts of the compounds of Formula I include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, pthalate, benzenesulfonate, toluenesulfonate, phenylacetate, citrate, lactate, maleate, tartarate, methanesulfonate, and the like. Also contemplated are salts of amino acids, such as arginate, gluconate and galacturonate salts and the like (see, for example, Berge et al., "Pharmaceutical Salts," *J. of Pharmaceutical Science*, 1977, 66, 1-19, which is incorporated herein by reference in its entirety).

The acid addition salts of compounds of Formula I can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are substantially equivalent to their respective free base for the purposes of the present invention.

Pharmaceutically acceptable base addition salts of compounds of Formula I can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chlorocaine, choline, diethanolamine, ethylenediamine, N-methylglucamine, and procaine (see, for example, Berge et al., supra).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are substantially equivalent to their respective free acid for the purposes of the present invention.

In one embodiment, compounds of the present invention are of the formula:

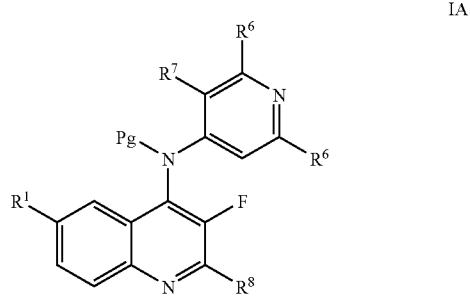

IA

In another embodiment, compounds of the present invention are of the formula:

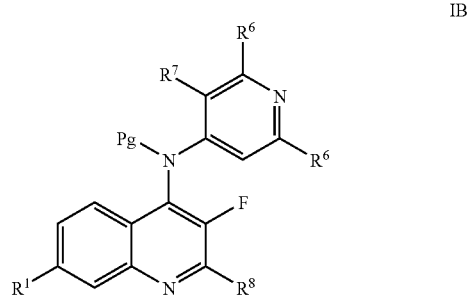

IB

Still in another embodiment, $R^8$ in compounds of Formulas I, IA and IB is selected from phenyl, naphthyl, pyridyl, thienyl, furyl (each of which is optionally substituted with 1-3 $R^5$), cyclohexyl, cyclopentyl, cyclopropyl, and t-butyl. When $R^8$ is a mono-substituted phenyl, the preferred substituent position on the phenyl ring is meta-position relative to the quinoline ring system. A particularly preferred $R^8$ is selected from 2-fluorophenyl, benzo[1,3]dioxol-5-yl, 2-trifluoromethylphenyl, 2-chlorophenyl, pyridin-4-yl, 2-methylphenyl, 2-methoxyphenyl, 3-fluorophenyl, 3-chlorophenyl, 5-chlorothiophen-2-yl, 5-chloro-furan-2-yl, 5-methyl-thiophen-2-yl, 5-methyl-furan-2-yl, 4-methyl-thiophen-2-yl, 2,3-dihydrobenzofuran-5-yl, 2-methylsulfanylphenyl, 4-fluorophenyl, 2-methanesulfonylphenyl, 4-methoxyphenyl, 2-cyanophenyl, 2-amidophenyl, 4-hydroxyphenyl, 3-aminophenyl, 3-methoxyphenyl, 4-cyanophenyl, 2,6-dichlorophenyl, phenyl, 4-chlorophenyl, cyclohexyl, cyclopropyl, cyclopentyl, 4-methylsulfanylphenyl, t-butyl, 4-amidophenyl, naphthalen-2-yl, 4-methanesulfonylphenyl, and 2-bromophenyl.

In another embodiment, $R^8$ in compounds of Formulas I, IA and IB is a 5-6 membered aryl or heteroaryl selected from phenyl, pyridyl, thienyl, and furyl, each of which is optionally substituted with 1-3 $R^5$.

Yet in another embodiment, each $R^1$ in compounds of Formulas I, IA and IB is independently selected from thienyl, furyl, pyrrolyl, and phenyl, each of which is optionally substituted with 1-3 $R^5$; halo; —$OR^4$; —$N(R^3)_2$; and —$N(R^3)$-T—$OR^4$. Particularly preferred $R^1$ are those shown in representative compounds of Formula I below, for example, methylamino, 2-methoxyethylamino, furanyl, thiophenyl (i.e., thienyl), phenyl optionally substituted with 1-3 $R^5$, halogen and methoxy. An especially preferred $R^1$ is independently selected from methylamino, 2-methoxyethylamino, furan-2-yl, thiophen-3-yl, phenyl optionally substituted with 1-2 $R^5$, bromo and methoxy.

Still further, combinations of the different embodiments and preferred groups described herein will form other embodiments and preferred groups. For example, one particularly preferred group of compounds of Formula I are those represented by Formula IA in which $R^1$ is selected from methylamino, 2-methoxyethylamino, optionally substituted phenyl, furan-2-yl and thiophen-3-yl. Still in another particular embodiment, a preferred group of compounds of Formula I are those represented by Formula IB in which $R^1$ is selected from methoxy, methylamino, 2-methoxyethylamino and bromo. In this manner, a variety of preferred compounds are embodied within the present invention.

Some of the representative compounds of Formula I are shown in Table 1 below.

TABLE 1

Representative compounds of Formula I.

(1)

[3-Fluoro-2-(2-methylsulfanyl-phenyl)-quinolin-4-yl]-pyridin-4-yl-amine

TABLE 1-continued

Representative compounds of Formula I.

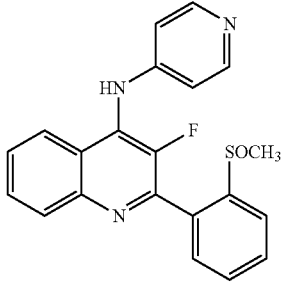

[3-Fluoro-2-(2-methanesulfinyl-
phenyl)-quinolin-4-yl]-pyridin-
4-yl-amine (2)

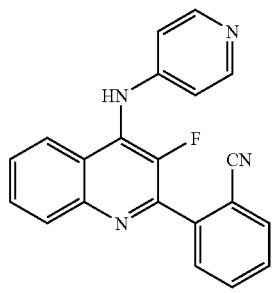

2-[3-Fluoro-4-(pyridin-4-
ylamino)-quinolin-2-yl]-
benzonitrile (3)

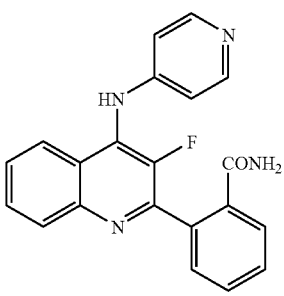

2-[3-Fluoro-4-(pyridin-4-
ylamino)-quinolin-2-yl]-
benzamide (4)

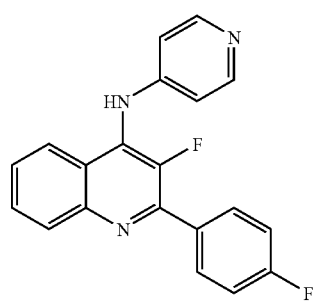

[3-Fluoro-2-(4-fluoro-phenyl)-
quinolin-4-yl]-pyridin-4-yl-amine (5)

TABLE 1-continued

Representative compounds of Formula I.

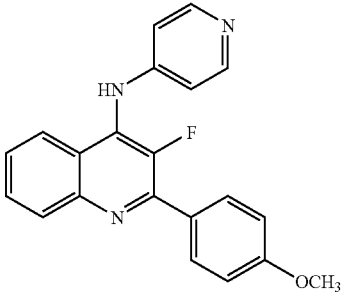

[3-Fluoro-2-(4-methoxy-phenyl)-quinolin-
4-yl]-pyridin-4-yl-amine (6)

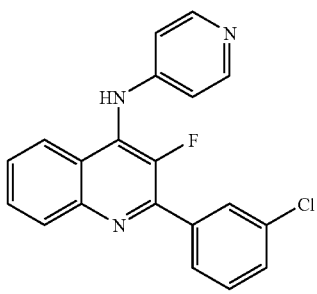

[2-(3-Chloro-phenyl)-3-fluoro-
quinolin-4-yl]-pyridin-4-yl-amine (7)

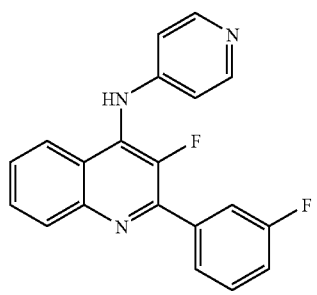

[3-Fluoro-2-(3-fluoro-phenyl)-
quinolin-4-yl]-pyridin-4-yl-amine (8)

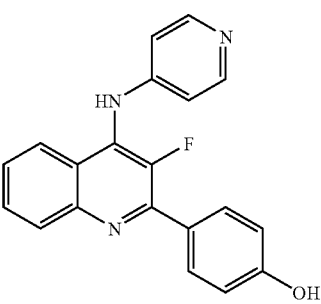

4-[3-Fluoro-4-(pyridin-4-ylamino)-
quinolin-2-yl]-phenol (9)

(10)

TABLE 1-continued

Representative compounds of Formula I.

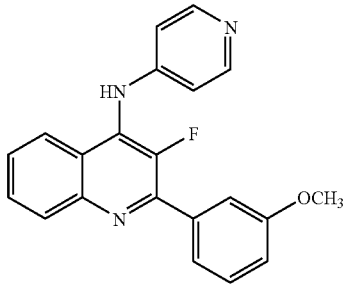

[3-Fluoro-2-(3-methoxy-phenyl)-
quinolin-4-yl]-pyridin-4-yl-amine

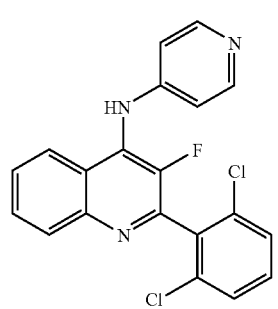
(11)

[2-(2,6-Dichloro-phenyl)-3-fluoro-
quinolin-4-yl]-pyridin-4-yl-amine

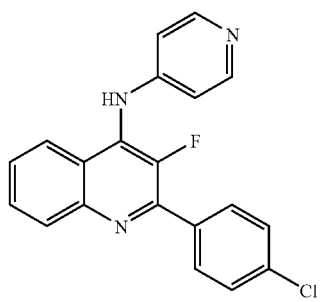
(12)

[2-(4-Chloro-phenyl)-3-fluoro-
quinolin-4-yl]-pyridin-4-yl-amine

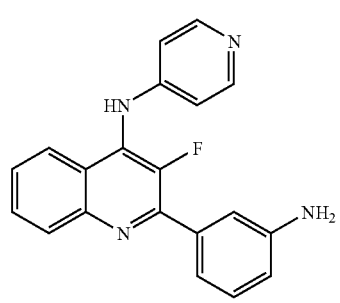
(13)

[2-(3-Amino-phenyl)-3-fluoro-quinolin-
4-yl]-pyridin-4-yl-amine

TABLE 1-continued

Representative compounds of Formula I.

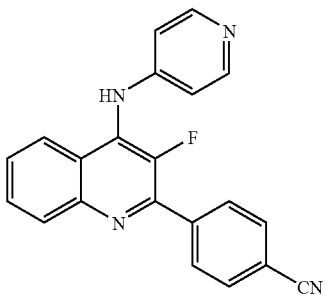
(14)

4-[3-Fluoro-4-(pyridin-4-ylamino)-
quinolin-2-yl]-benzonitrile

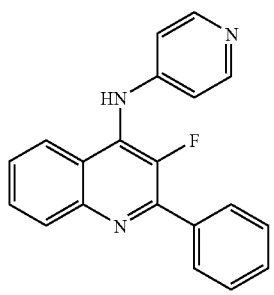
(15)

(3-Fluoro-2-phenyl-quinolin-4-
yl)-pyridin-4-yl-amine

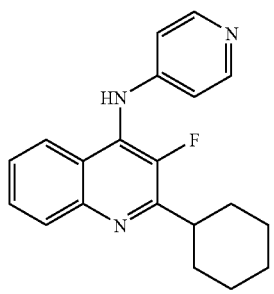
(16)

(2-Cyclohexyl-3-fluoro-quinolin-
4-yl)-pyridin-4-yl-amine

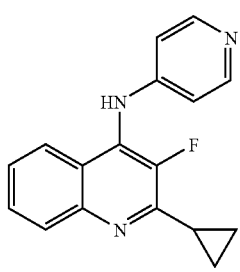
(17)

(2-Cyclopropyl-3-fluoro-quinolin-
4-yl)-pyridin-4-yl-amine

TABLE 1-continued

Representative compounds of Formula I.

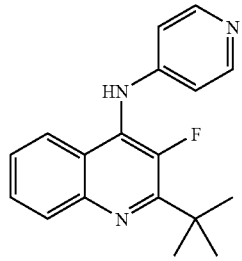

(18)

(2-tert-Butyl-3-fluoro-quinolin-
4-yl)-pyridin-4-yl-amine

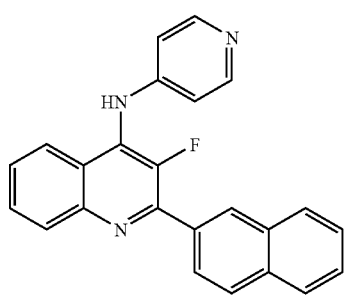

(19)

(3-Fluoro-2-naphthalen-2-yl-
quinolin-4-yl)-pyridin-4-yl-amine

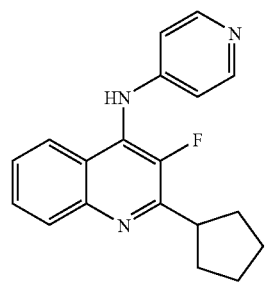

(20)

(2-Cyclopentyl-3-fluoro-quinolin-
4-yl)-pyridin-4-yl-amine

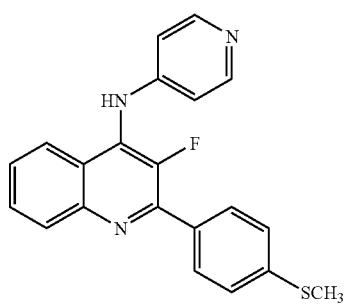

(21)

[3-Fluoro-2-(4-methylsulfanyl-phenyl)-
quinolin-4-yl]-pyridin-4-yl-amine

TABLE 1-continued

Representative compounds of Formula I.

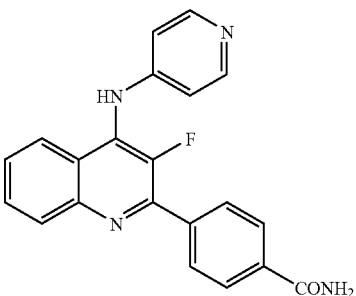

(22)

4-[3-Fluoro-4-(pyridin-4-ylamino)-
quinolin-2-yl]-benzamide

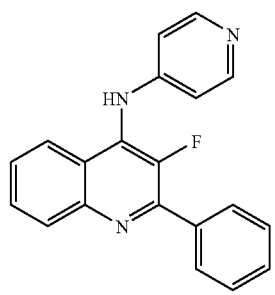

(23)

(3-Fluoro-2-phenyl-quinolin-4-yl)-
pyridin-4-yl-amine

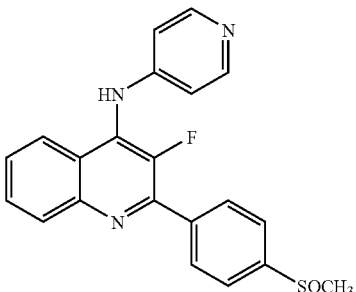

(24)

[3-Fluoro-2-(4-methanesulfinyl-phenyl)-
quinolin-4-yl]-pyridin-4-yl-amine

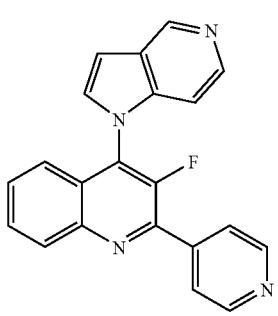

(25)

3-Fluoro-2-pyridin-4-yl-4-
pyrrolo[3,2-c]pyridin-1-yl-quinoline

TABLE 1-continued

Representative compounds of Formula I.

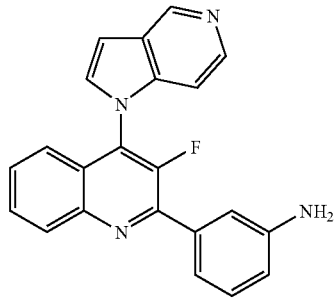 (26)

3-(3-Fluoro-4-pyrrolo[3,2c]pyridin-
1-yl-quinolin-2-yl)-phenylamine

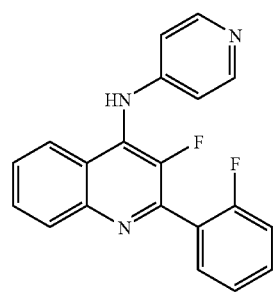 (27)

[3-Fluoro-2-(2-fluoro-phenyl)-
quinolin-4-yl]-pyridin-4-yl-amine

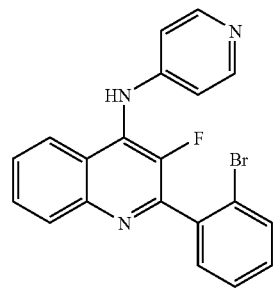 (28)

[2-(2-Bromo-phenyl)-3-fluoro-
quinolin-4-yl]-pyridin-4-yl-amine

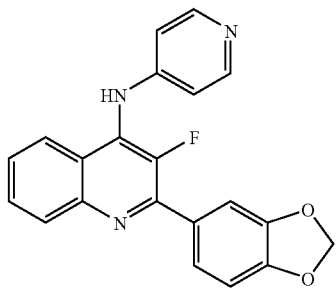 (29)

(2-Benzo[1,3]dioxol-5-yl-3-fluoro-
quinolin-4-yl)-pyridin-4-yl-amine

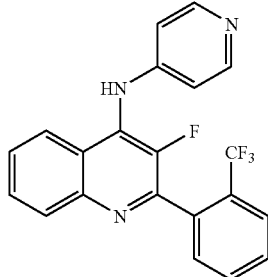 (30)

[3-Fluoro-2-(2-trifluoromethyl-
phenyl)-quinolin-4-yl]-pyridin-
4-yl-amine

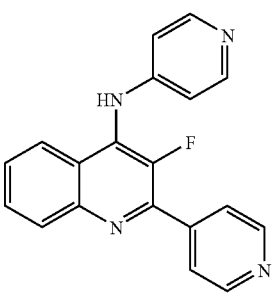 (31)

(3-Fluoro-2-pyridin-4-yl-quinolin-
4-yl)-pyridin-4-yl-amine

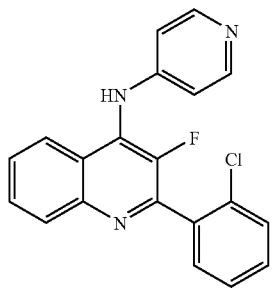 (32)

[2-(2-Chloro-phenyl)-3-fluoro-
quinolin-4-yl]-pyridin-4-yl-amine

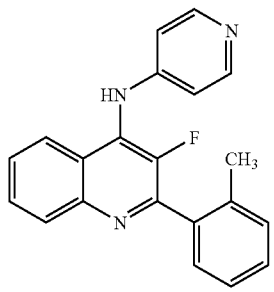 (33)

(3-Fluoro-2-o-tolyl-quinolin-4-
yl)-pyridin-4-yl-amine

TABLE 1-continued

Representative compounds of Formula I.

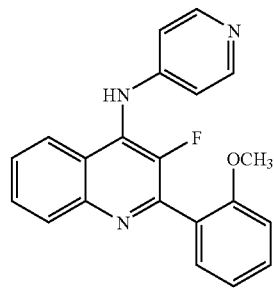

(34)

[3-Fluoro-2-(2-methoxy-phenyl)-
quinolin-4-yl]-pyridin-4-yl-amine

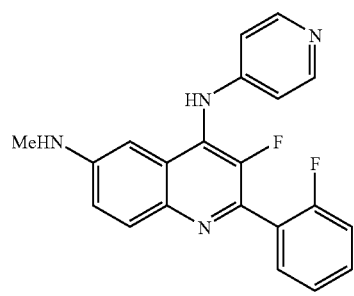

(35)

3-Fluoro-2-(2-fluoro-phenyl)-$N^6$-methyl-$N^4$-
pyridin-4-yl-quinoline-4,6-diamine

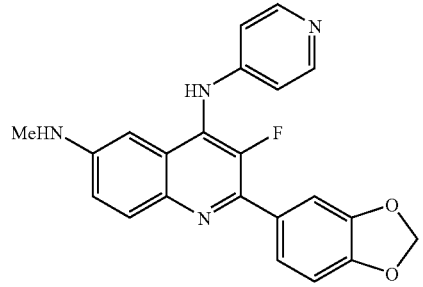

(36)

2-Benzo[1,3]dioxol-5-yl-3-fluoro-$N^6$-methyl-
$N^4$-pyridin-4-yl-quinoline-4,6-diamine

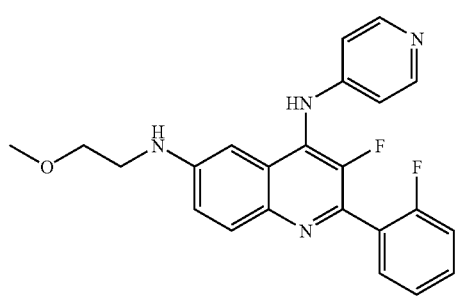

(37)

3-Fluoro-2-(2-fluoro-phenyl)-$N^6$-(2-methoxy-
ethyl)-$N^4$-pyridin-4-yl-quinoline-4,6-diamine TABLE 1-continued Representative compounds of Formula I.

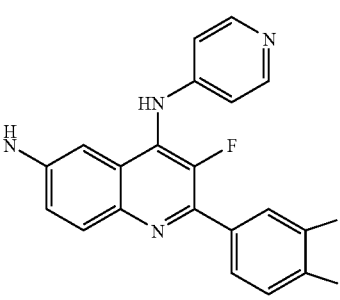

(38)

2-Benzo[1,3]dioxol-5-yl-3-fluoro-$N^6$-(2-methoxy-
ethyl)-$N^4$-pyridin-4-yl-quinoline-4,6-diamine

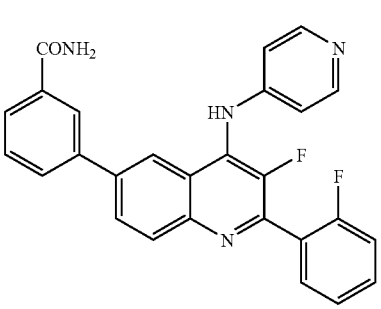

(39)

3-[3-Fluoro-2-(2-fluoro-phenyl)-4-(pyridin-
4-ylamino)-quinolin-6-yl]-benzamide

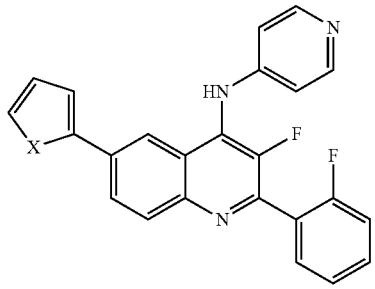

(40)

X = S, O, NH
When X = O,

[3-Fluoro-2-(2-fluoro-phenyl)-6-furan-2-yl-
quinolin-4-yl]-pyridin-4-yl-amine

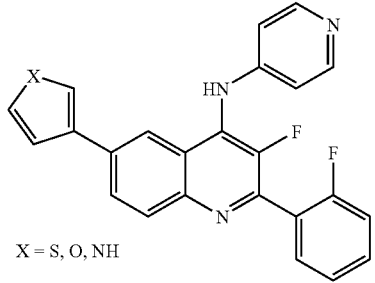

(41)

X = S, O, NH

When X = S,
[3-Fluoro-2-(2-fluoro-phenyl)-6-thiophen-3-
yl-quinolin-4-yl]-pyridin-4-yl-amine TABLE 1-continued Representative compounds of Formula I.

(42)
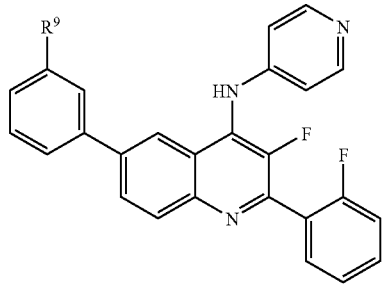

R⁹ = C₁₋₃ alkyl, halo, —OH, N(R³)₂, cyano, or —OR⁴, where R³ and R⁴ are as defined herein

(43)
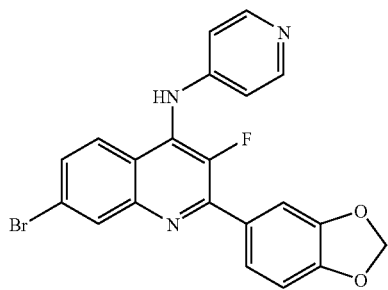

(2-Benzo[1,3]dioxol-5-yl-7-bromo-3-fluoro-quinolin-4-yl)-pyridin-4-yl-amine

(44)
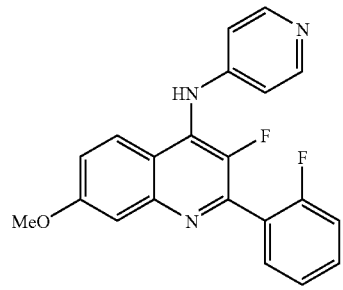

[3-Fluoro-2-(2-fluoro-phenyl)-7-methoxy-quinolin-4-yl]-pyridin-4-yl-amine

(45)
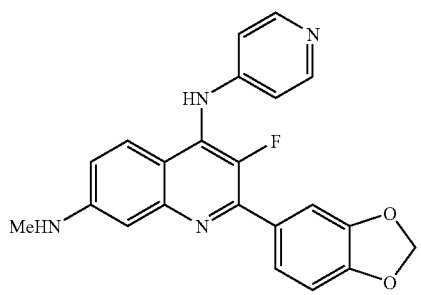

2-Benzo[1,3]dioxol-5-yl-3-fluoro-N⁷-methyl-N⁴-pyridin-4-yl-quinoline-4,7-diamine

(46)
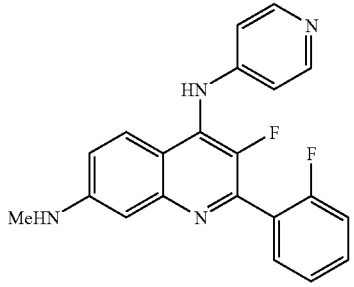

3-Fluoro-2-(2-fluoro-phenyl)-N⁷-methyl-N⁴-pyridin-4-yl-quinoline-4,7-diamine

(47)
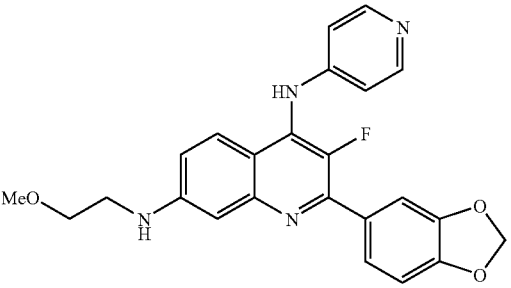

2-Benzo[1,3]dioxol-5-yl-3-fluoro-N⁷-(2-methoxy-ethyl)-N⁴-pyridin-4-yl-quinoline-4,7-diamine

(48)
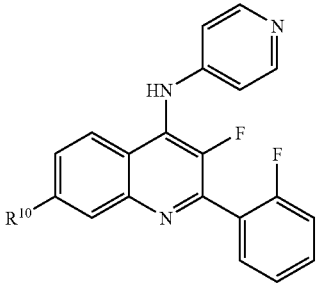

R¹⁰ is independently selected from thienyl, furyl, pyrrolyl, and phenyl, each of which is optionally substituted with 1-3 R⁵; halo; —OR⁴; —N(R³)₂; and —N(R³)—T—OR⁴, where R³, R⁴, R⁵ and T are as defined herein. Particularly preferred R¹⁰ is methylamino, 2-methoxyethylamino, furanyl, thiophenyl (i.e., thienyl), phenyl optionally substituted with 1-3 R⁵, halogen or methoxy.

(49)
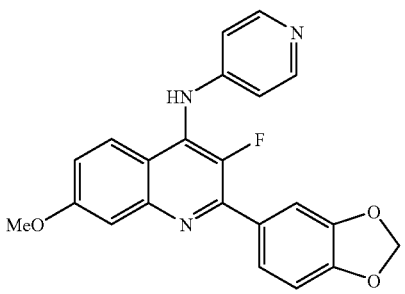

(2-Benzo[1,3]dioxol-5-yl-3-fluoro-7-methoxy-quinolin-4-yl)-pyridin-4-yl-amine

TABLE 1-continued

Representative compounds of Formula I.

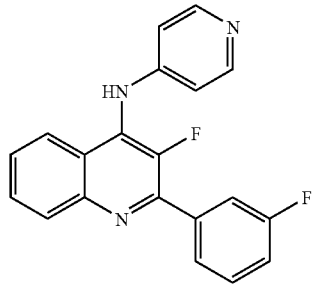

(50)

[3-Fluoro-2-(3-fluoro-phenyl)-
quinolin-4-yl]-pyridin-4-yl-amine

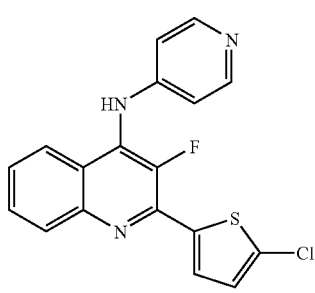

(51)

[2-(5-Chloro-thiophen-2-yl)-3-
fluoro-quinolin-4-yl]-pyridin-4-yl-
amine

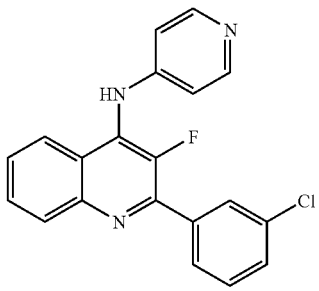

(52)

[2-(3-Chloro-phenyl)-3-fluoro-
quinolin-4-yl]-pyridin-4-yl-amine

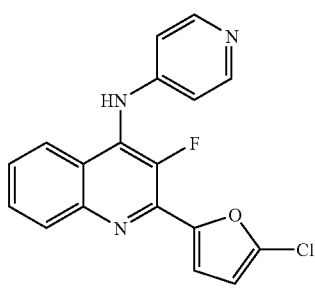

(53)

[2-(5-Chloro-furan-2-yl)-3-
fluoro-quinolin-4-yl]-pyridin-4-yl-amine

TABLE 1-continued

Representative compounds of Formula I.

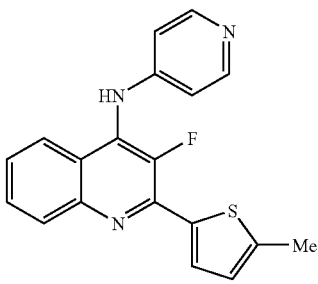

(54)

[3-Fluoro-2-(5-methyl-thiophen-2-yl)-
quinolin-4-yl]-pyridin-4-yl-amine

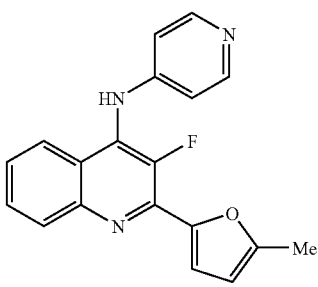

(55)

[3-Fluoro-2-(5-methyl-furan-2-yl)-
quinolin-4-yl]-pyridin-4-yl-amine

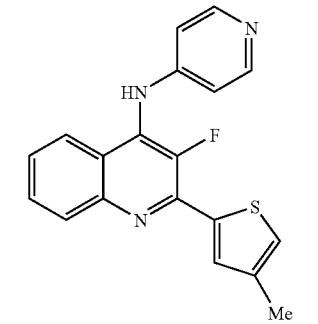

(56)

[3-Fluoro-2-(4-methyl-thiophen-2-yl)-
quinolin-4-yl]-pyridin-4-yl-amine

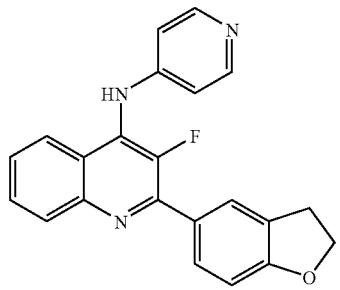

(57)

[2-(2,3-Dihydro-benzofuran-5-yl)-3-
fluoro-quinolin-4-yl]-pyridin-4-yl-amine

TABLE 1-continued

Representative compounds of Formula I.

(58)

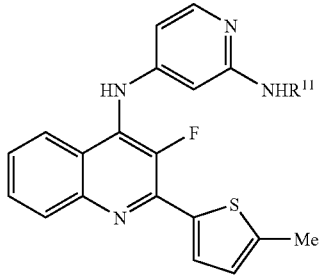

where R[11] = alkyl, benzyl, or phenyl (59)

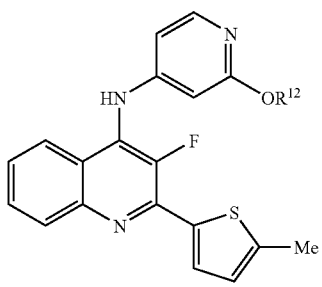

where R[12] = H, Me, or
—CH$_2$CH$_2$-piperidine (60)

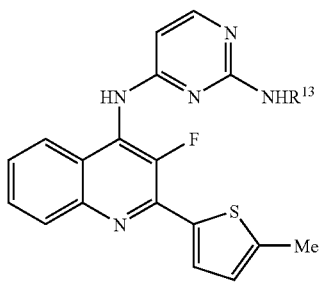

where R[13] = alkyl, benzyl, phenyl or
alkyloxy (61)

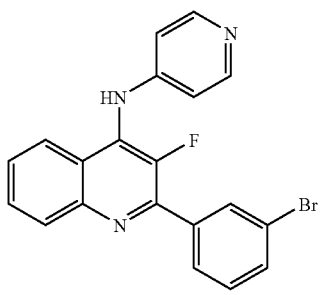

[2-(3-Bromo-phenyl)-3-fluoro-
quinolin-4-yl]-pyridin-4-yl-amine

TABLE 1-continued

Representative compounds of Formula I.

(62)

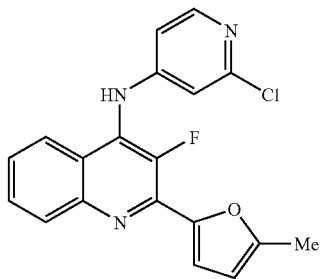

(2-Chloro-pyridin-4-yl)-[3-(fluoro-2-
(5-methyl-furan-2-yl)-quinolin-4-yl]-
amine (63)

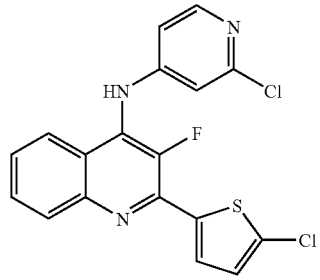

(2-Chloro-pyridin-4-yl)-[2-(5-chloro-
thiophen-2-yl)-3-fluoro-quinolin-4-yl]-
amine (64)

(2-Chloro-pyridin-4-yl)-[3-fluoro-2-
(3-fluoro-phenyl)-quinolin-4-yl]-
amine

TABLE 1-continued

Representative compounds of Formula I.

(65)

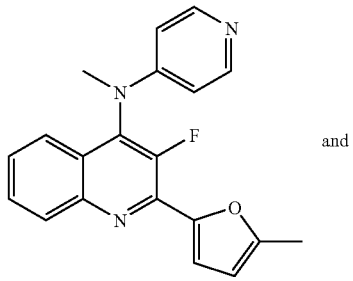

[3-Fluoro-2-(5-methyl-furan-2-yl)-quinolin-4-yl]-methyl-pyridin-4-yl-amine and (66)

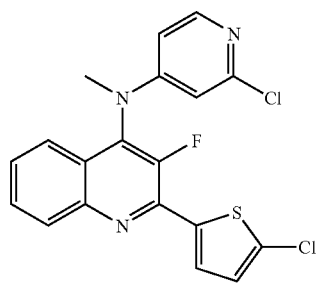

(2-Chloro-pyridin-4-yl)-[2-(5-chloro-thiophen-2-yl)-3-fluoro-quinolin-4-yl]-methyl-amine Synthesis The compounds of the present invention may be synthesized by a variety of methods known to one of ordinary skill in the art or depicted in the illustrative synthetic reaction schemes shown and described below. Starting materials used in any of these methods are commercially available from chemical vendors such as Aldrich, Sigma, Nova Biochemicals, Bachem Biosciences, and the like, or can be prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

It should be appreciated that the following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

The starting materials and the intermediates of the synthetic reaction schemes can be isolated and purified, if desired, using conventional techniques, including but not limited to, filtration, distillation, crystallization, chromatography, and the like. Such materials can be characterized using conventional means, including physical constants and spectral data.

Scheme 1

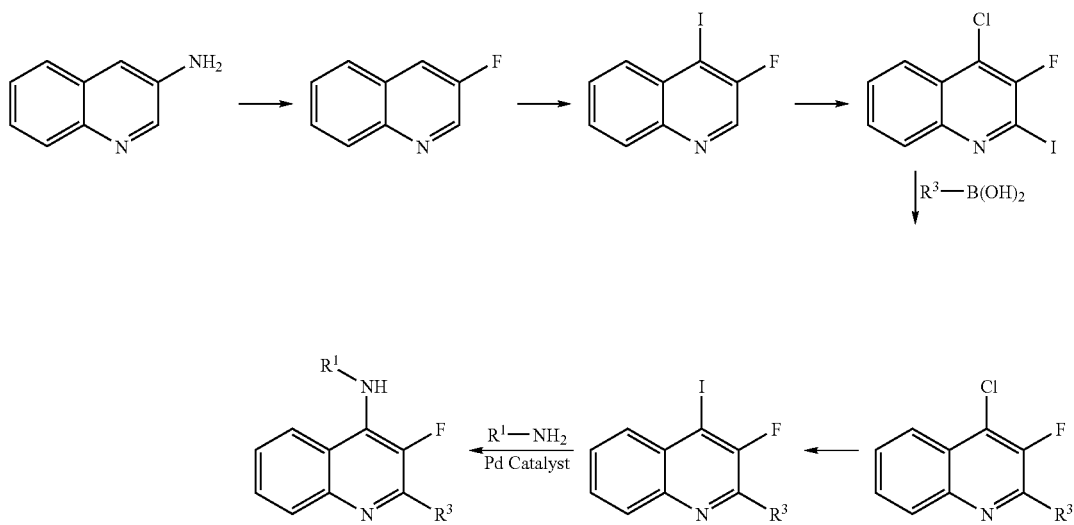

As shown in Scheme 1 above, 3-aminoquinoline was converted to 3-fluoroquinoline. This conversion is typically achieved by converting the amino group to a diazonium salt and displacing the diazonium moiety with a fluoride ion. Lithiation of 3-fluoroquinoline with a strong base, e.g., lithium diisopropyl amide, followed by treatment with iodine gave 3-fluoro-4-iodoquinoline. Deprotonation of 3-fluoro-4-iodoquinoline with a base, e.g., lithium diisopropyl amide, and reacting the deprotonated moiety with hexachloroethane gave 4-chloro-3-fluoro-2-iodoquinoline. Reacting 4-chloro-3-fluoro-2-iodoquinoline with a boronic acid derivative $R^3$—$B(OH)_2$ gave the 2-substituted quinoline compound. A metal halogen exchange reaction between the 2-substituted quinoline compound and butyl lithium followed by quenching with iodine then gave a 2-substituted-3-fluoro-3-iodoquinoline compound, which was subjected to a palladium mediated cross-coupling reaction with an amine compound, e.g., $R^1$—$NH_2$, to yield the desired compound.

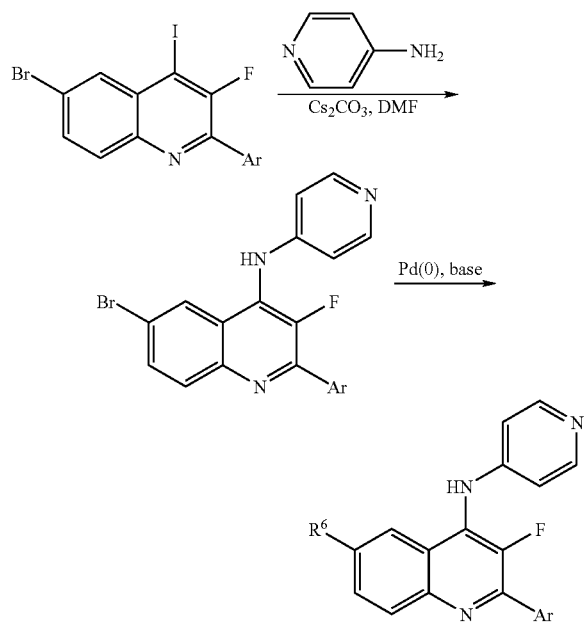

Scheme 2

As shown in Scheme 2, instead of using a palladium catalyst mediated cross-coupling reaction, the iodo group on the 4-position of the quinoline compound can also be displaced with an amino compound. For example, reacting a 2-aryl-6-bromo-3-fluoro-4-iodoquinoline compound with 4-aminopyridine in the presence of a base gave a [2-aryl-6-bromo-3-fluoroquinolin-4-yl]pyridyl-4-yl amine compound, which can be further modified by reacting with a various amino compounds, arylboronic acids or heteroaryl boronic acids using a palladium mediated cross-coupling reaction to afford the desired 6-substituted-2-aryl-3-fluoroquinoline compounds.

Utility

Compounds of the present invention possess a wide variety of biological activities. In particular, compounds of the present invention are useful in modulating, especially inhibiting, TGF-β signaling pathway. Accordingly, compounds of the present invention are useful in treating a patient having a TGF-β mediated disorder. Treatment of such a patient generally involves administering a therapeutically effective amount of a compound of Formula I to the patient in need of such a treatment.

As used herein, a subject or a patient can be any mammal, so long as the mammal is in need of modulation of a pathological or biological process mediated by compounds of the present invention. The term 'mammal' is defined as a species belonging to the class Mammalia. Examples of mammals include mice, rats, cows, sheep, pigs, goats, horses, bears, monkeys, dogs, cats and, preferably, humans. Transgenic organisms which express TGF-β are also included in this definition.

TGF-β is a potent regulator of the cell cycle in many cell types including vascular smooth muscle (VSM) and endothelial cells and, as a result, TGF-β is believed to play an important role in vascular proliferative process such as angiogenesis. Pathological conditions associated with VSM include restenosis, atherosclerosis, coronary heart disease, thrombosis, myocardial infarction, stroke, smooth muscle neoplasms such as leiomyoma and leiomyosarcoma of the bowel and uterus, uterine fibroid or fibroma, and obliterative disease of vascular grafts and transplanted organs. Other vascular diseases include unstable angina, chronic stable angina, transient ischemic attacks, strokes, peripheral vascular disease, preeclampsia, deep venous thrombosis, embolism, disseminated intravascular coagulation or thrombotic cytopenic purpura. Vascular injury includes an injury arising by any means including, but not limited to, procedures such as angioplasty, carotid endarterectomy, post CABG (coronary artery bypass graft) surgery, vascular graft surgery, stent placements or insertion of endovascular devices and prostheses.

Compounds of the present invention can be used to treat smooth muscle cell proliferation. In one particular embodiment, a compound of the present invention is used to inhibit or reduce stenosis due to proliferation of vascular smooth muscle cells following traumatic injury to vessels such as during vascular surgery. The present invention also contemplates the delivery of a compound of Formula I to vascular smooth muscle cells to exert inhibitory effects over an extended period of time.

The TGF-β inhibition activity is useful in treating fibroproliferative diseases, treating collagen vascular disorders, treating eye diseases associated with a fibroproliferative condition, venting excessive scarring, treating neurological conditions and other conditions that are targets for TGF-β inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations. Neurological conditions characterized by TGF-β production include CNS injury after traumatic and hypoxic insults, Alzheimer's disease, and Parkinson's disease.

Other conditions that are potential clinical targets for TGF-β inhibitors include myelofibrosis, tissue thickening resulting from radiation treatment, nasal polyposis, polyp surgery, liver cirrhosis, and osteoporosis.

The phrase "TGF-β disease condition" includes those states, disorders, or diseases characterized by aberrant or undesirable activity or expression of TGF-β. Examples of TGF-β associated disease conditions include, but are not limited to, disorders involving or associated with cardiovascular diseases such as myocardial infarction, stroke, thrombosis, congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporine, HIV-associated nephropathy, transplant nephropathy, chronic urethral obstruction; hepatic diseases associated with excessive scarring and progressive sclerosis, including cirrhosis due to all etiologies, disorders of the biliary tree, and hepatic dysfunction attributable to infections, such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGF-β production or enhanced sensitivity to TGF-β, including states post-traumatic or hypoxic injury, Alzheimer's disease, and Parkinson's disease; and diseases of the joints involving scarring sufficient to impede mobility or produce pain, including states post-mechanical or surgical trauma, osteoarthritis and rheumatoid arthritis.

The modulation of immune and inflammation systems by TGF-β includes stimulation of leukocyte recruitment, cytokine production, and lymphocyte effector function, and inhibition of T-cell subset proliferation, β-cell proliferation, antibody formation, and monocytic respiratory burst. Wahl et al., *Immunol Today*, 1989, 10, 258-61. TGF-β plays an important role in the pathogenesis of lung fibrosis which is a major cause of suffering and death seen in pulmonary medicine based on its strong extracellular matrix inducing effect. The association of TGF-β with human lung fibrotic disorders has been demonstrated in idiopathic pulmonary fibrosis, autoimmune lung diseases and bleomycin induced lung fibrosis. Nakao et al., *J. Clin. Inv.*, 1999, 104, 5-11.

Other TGF-β disease states include inhibition of the intracellular signaling pathway such as fibroproliferative diseases, including kidney disorders associated with unregulated TGF-β activity and excessive fibrosis, including glomerulonephritis (GN), such as mesangial proliferative GN, immune GN, and crescentic GN. Other renal conditions that can be treated by inhibitors of TGF-β intracellular signaling pathway include diabetic nephropathy, renal interstitial fibrosis, renal fibrosis in transplant patients receiving cyclosporine, and HIV-associated nephropathy. Collagen vascular disorders that can be treated by inhibitors of TGF-β intracellular signaling pathway include progressive systemic sclerosis, polymyositis, scleroderna, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Eye diseases associated with a fibroproliferative condition include retinal reattachment surgery accompanying proliferative vitreoretinopathy, cataract extraction with intraocular lens implantation, and post glaucoma drainage surgery.

In addition to the disease states noted above, other diseases treatable or preventable by the administration of compounds or pharmaceutically acceptable salts thereof of the present invention include, but not limited to, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life threatening thrombi occurring throughout the microvasculature leading to widespread organ failure, hemmorhagic stroke, renal dialysis, blood oxygenation and cardiac catherization.

Compounds of the present invention can also be used in transcatheter vascular therapies (TVT) including angioplasty, e.g., laser angioplasty and percutaneous transluminal coronary angioplasty (PTCA) procedures employing balloon catheters, and indwelling catheters; vascular grafting using natural or synthetic materials, such as in saphenous vein coronary bypass grafts, dacron and venous grafts used for peripheral arterial reconstruction, etc.; placement of a mechanical shunt, such as a PTFE hemodialysis shunt used for arteriovenous communications; placement of an intravascular stent, which may be metallic, plastic or a biodegradable polymer; or delivery of the compounds or pharmaceutically acceptable salt thereof to the lumen of a vessel via catheter, before, during or after angioplasty. See Schatz, U.S. Pat. No. 5,195,984; Palmaz, U.S. Pat. No. 4,739,762, the disclosures of which are incorporated herein by reference.

Compounds of the present invention can also be incorporated as a coating on medical devices, such as stents, to prevent thrombus formation and to control smooth muscle cell proliferation.

The stent or shunt useful in the method of the present invention can comprise a biodegradable coating or porous non-biodegradable coating, having dispersed therein a sustained-release dosage form of the compound or pharmaceutically acceptable salts thereof as a therapeutic agent. In an alternative embodiment, a biodegradable stent or shunt may also have the therapeutic agent impregnated in the stent or shunt matrix. Also contemplated is the use of a biodegradable stent or shunt with the therapeutic agent impregnated therein which is further coated with a biodegradable coating or with a porous non-biodegradable coating having a sustained release-dosage form dispersed therein. This embodiment of the invention provides a differential release rate of the therapeutic agent, i.e., there is a faster release of the therapeutic agent from the coating followed by delayed release of the therapeutic agent that was impregnated in the stent or shunt matrix upon degradation of the stent or shunt matrix. The intravascular stent or shunt provides a mechanical means of maintaining or providing an increase in luminal area of a vessel, and the antiproliferative agent inhibits the vascular smooth muscle cell proliferative response induced by the stent or shunt, which can cause occlusion of blood flow and coronary failure.

Compounds of the present invention can also be used to inhibit vascular smooth muscle cell proliferation associated with procedural vascular trauma due to organ transplantation, vascular surgery, angioplasty, shunt placement, stent placement or vascular grafting. This aspect of the invention generally comprises administering to a mammal, such as a human, that is subjected to the procedural trauma an effective antiproliferative amount of a compound of Formula I. Administration of compound of Formula I can be systemic, as by oral or parenteral administration, or local, as to the site of the vascular trauma, or both.

Compounds of the present invention can be used alone or in combination with other therapeutic or diagnostic agents. In certain preferred embodiments, the compounds of the invention are coadministered with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. In some instances, compounds of the present invention allow for reduced doses of the thrombolytic agents to be used, and therefore minimize potential hemorrhagic side-effects.

In one particular embodiment, preferred compounds of Formula I are those that inhibit the phosphorylation of smad2 or smad3 by modulating TGF-$\beta$ type I or activin like kinase (ALK5) receptor. A particularly preferred group of compounds of Formula I are those having $IC_{50}$ of about 100 $\mu$M or less, with those having $IC_{50}$ of about 10 $\mu$M or less being more particularly preferred. Especially preferred compounds of Formula I are those having $IC_{50}$ of about 1 $\mu$M or less.

Administration and Pharmaceutical Composition

Another aspect of the present invention provides a pharmaceutical composition comprising at least one compound of the present invention together with at least one pharmaceutically acceptable carrier (or excipient), and optionally other therapeutic and/or prophylactic ingredients.

Pharmaceutically acceptable carriers (or excipients) for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Compounds of the present invention can be administered in a therapeutically effective amount by any of the accepted modes of administration for agents that serve similar utilities. The therapeutically effective amount of the compound of the present invention can range broadly depending upon the desired affects and the therapeutic indication. Therapeutically effective dosages can be determined by either in vitro or in vivo methods. For each particular compound of the present invention, individual determinations can be made to determine the optimal dosage required. The range of therapeutically effective dosages is influenced by a variety of factors, such as the route of administration, the therapeutic objectives, nature of the condition, the severity of the condition, the particular subject to be treated, and the judgment of the practitioner.

The formulation will also depend on mode of administration. As the compounds of the present invention are small molecules, they are conveniently administered orally by compounding them with suitable pharmaceutical excipients so as to provide tablets, capsules, syrups, and the like. Suitable formulations for oral administration can also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

For injection by hypodermic needle, it may be assumed the dosage is delivered into the body's fluids. For other routes of administration, the absorption efficiency is typically determined for each individual compound by methods well known in pharmacology. Accordingly, it may be necessary for the therapist to titer the dosage and modify the route of administration as required to obtain the desired therapeutic effect. The determination of effective dosage levels, that is, the dosage levels necessary to achieve the desired result, can be readily determined by one skilled in the art. Typically, applications of compound are commenced at lower dosage levels, with dosage levels being increased until the desired effect is achieved.

The compounds useful in the invention can also be administered through suppositories or other transmucosal vehicles. Typically, such formulations include excipients that facilitate the passage of the compound through the mucosa such as pharmaceutically acceptable detergents. The compounds can also be administered topically, for topical conditions, or in formulation intended to penetrate the skin. These include lotions, creams, ointments and the like which can be formulated by known methods in the art.

Compounds of the present invention can also be administered by injection, including intravenous, intramuscular, subcutaneous or intraperitoneal injection. Typical formulations for such use are liquid formulations in isotonic vehicles such as Hank's solution or Ringer's solution. Alternative formulations include nasal sprays, liposomal formulations, slow-release formulations, and the like, as are known in the art.

The dosages of the compounds of the invention depend on a number of factors which can vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will likely vary, however, depending on the conditions being treated and the judgment of the practitioner. It should be noted that the compounds of Formula I can be administered as individual active ingredients, or as mixtures of several embodiments of this formula. In addition, the inhibitors of TGF-$\beta$ can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

The biological properties of the compounds of the present invention can be readily characterized by methods that are well known in the art such as, for example, by in vitro protease activity assays and in vivo studies to evaluate antithrombotic efficacy, and effects on hemostasis and hematological parameters, such as are illustrated in the examples.

Diagnostic applications of the compounds of the invention will typically utilize formulations in the form of solutions or suspensions. In the management of thrombotic disorders, the compounds of the invention can be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of the invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol. The compounds of the invention can be administered parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which can be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3-11, more preferably 5-9 and most preferably 7-8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

Compounds of the invention can also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

Compounds of this invention can also be delivered by the use of antibodies, antibody fragments, growth factors, hormones, or other targeting moieties, to which the compound molecules are coupled. Compounds of this invention can also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

EXAMPLES

Additional objects, advantages, and novel features of this invention will become apparent to those skilled in the art upon examination of the following examples thereof. It should be appreciated that these examples are not to be considered as limiting the scope of the invention, but merely as being illustrative and representative thereof.

Example 1

Preparation of [3-fluoro-2-(2-fluoro-phenyl)-quinolin-4-yl]-pyridin-4-yl-amine

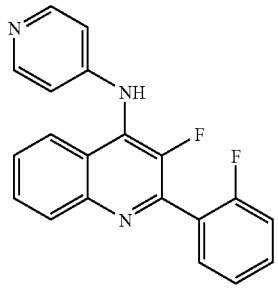

Step A: Preparation of 3-diazoquinoline

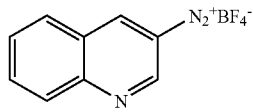

3-Aminoquinoline (10 g, 69 mmol) was dissolved in 70 mL of conc. HCl in a 250 mL round bottomed flask and cooled to 0° C. Sodium nitrite (9.6 g, 139 mmol) in 20 mL water was added drop wise over 0.5 h while maintaining the reaction temperature between 0-5° C. After stirring for another 0.5 h, fluoroboric acid (20 mL) was added and the stirring continued for another 0.5 h. The solid was filtered and dried under vacuum to yield the title compound (15.2 g, 90%).

Step B. Preparation of 3-fluoroquinoline

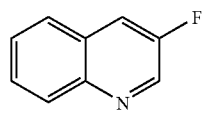

The tetrafluoroborate salt from Step A was suspended in 100 mL of toluene in 250 mL round bottomed flask equipped with a magnetic stirrer and heated to 110° C. An exothermic reaction occurred and the flask was maintained at that temperature until the evolution of gas stopped. The solvent was removed and the residue was basified to pH 7 using potassium carbonate. The resulting solution was extracted with 3×50 mL of ethyl acetate, and the organic layers were combined, dried over magnesium sulfate and concentrated in a rotary evaporator. The crude compound was purified by silica gel column chromatography using 9:1 hexane:ethyl acetate to yield the title compound (6.3 g, 68%). MS (ES) 148.1 (M+H)⁺.

Step C: Preparation of 3-fluoro-4-iodo-quinoline

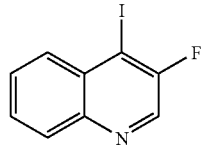

To a 0° C. solution of diisopropyl amine (2.8 mL, 27 mmol) in tetrahydrofuran (80 mL) was added dropwise butyl lithium (8.1 mL, 2.5 M solution in hexane, 27 mmol). After 10 min., the flask was cooled to −78° C. and 3-fluoro quinoline from Step B (3 g, 20 mmol) in 20 mL of tetrahydrofuran was added over 15 min. period. The stirring was continued for an additional 4 h., after which iodine (5.4 g, 21 mmol) in 10 mL of THF (tetrahydrofuran) was added and the reaction temperature was maintained at −78° C. for additional 2 h. The reaction was quenched by adding a mixture of water and tetrahydrofuran (25 mL, 1:9), and the resulting solution was extracted with ethyl acetate. The organic layers were combined, washed with water and brine. Purification by silica gel column gave the title compound (2.26 g, 40%). MS (ES) 148.1 (M+H)⁺.

Step D. Preparation of 4-chloro-3-fluoro-2-iodo-quinoline

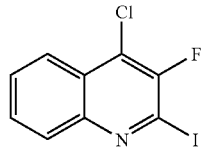

To a 0° C. solution of diisopropyl amine (0.215 mL, 2.1 mmol) in THF (5 mL) was added drop wise a solution of butyl lithium (0.615 mL, 2.5 M solution in hexane, 2.1 mmol). After 10 min. the flask was cooled to −78° C. and a solution of 3-fluoro-4-iodo-quinoline (from Step C, 0.412 g, 1.5 mmol) in 2 mL of tetrahydrofuran was added over 5 min. The stirring was continued for an additional 2 h., after which a solution of hexachloroethane (0.356 g, 1.5 mmol) in 1 mL of tetrahydrofuran was added and the reaction mixture was stirred at −78° C. for additional 2 h. The reaction mixture was diluted with a mixture of water and tetrahydrofuran (10 mL, 1:9) and extracted with ethyl acetate. The organic layers were combined, washed with water and brine, and purified by silica gel column chromatography to yield the title compound (0.318 g, 70%). MS (ES) 308.1 (M+H)⁺.

Step E: Preparation of 4-chloro-3-fluoro-2-(2-fluoro-phenyl)-quinoline

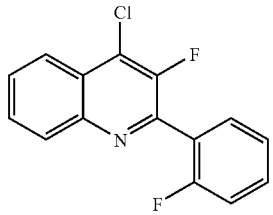

To a solution of 4-chloro-3-fluoro-2-iodo-quinoline (from step D, 0.3 g, 0.9 mmol) in toluene (5 mL) was added n-butanol (2 mL), water (3 mL) and cesium carbonate (1.14 g, 3.5 mmol). The resulting mixture was degassed for 5 min. and tetrakis(triphenyl-phosphine)palladium(0) (5 mg, 5 mol %)

and 2-fluorophenyl boronic acid (0.286 g, 2 mmol) were added. The reaction mixture was heated to 50° C. for 24 h., after which it was extracted with ethyl acetate. The organic layer was dried and concentrated in a rotary evaporator. The residue was purified by silica gel column chromatography using ethyl acetate/hexane gradient to yield the title compound (0.160 g, 48%). MS (ES) 336.1 (M+H)$^+$.

Step F: Preparation of
3-fluoro-2-(2-fluoro-phenyl)-4-iodo-quinoline

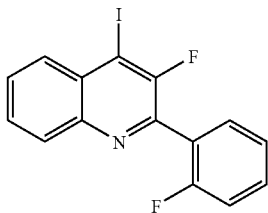

To a solution of 4-chloro-3-fluoro-2-(2-fluoro-phenyl)-quinoline (from step E, 0.160 g, 0.47 mmol) in tetrahydrofuran (3 mL) at −78° C. was added butyl lithium (0.6 mL, 2.5 M in hexane, 1.3 mmol). The mixture was stirred for 3 h. and iodine (0.148 g, 0.58 mmol) in 0.8 mL of THF was added. The reaction mixture was stirred for an additional 2 h. The reaction mixture was diluted with water (20 mL) and extracted with ethyl acetate (2×25 mL). The organic layers were combined, dried over sodium sulfate, concentrated and purified by silica gel column chromatography to yield the title compound (0.148 g, 84%). MS (ES) 368.1 (M+H)$^+$.

Step G. Preparation of [3-fluoro-2-(2-fluoro-phenyl)-quinolin-4-yl]-pyridin-4-yl-amine To a solution of 3-fluoro-2-(2-fluoro-phenyl)-4-iodo-quinoline (from Step F, 0.02 g, 0.05 mmol) in toluene (1 mL) was added S-BINAP (0.007 g, 0.01 mmol), sodium tert-butoxide (0.105 g, 1 mmol) and 4-aminopyridine (0.015 g, 0.05 mmol). The resulting mixture was degassed for 5 min., after which tris(dibenzylidineacetone) dipalladium(0) (0.0025 g, 0.0025 mmol) was added. The reaction mixture was heated to 110° C. for 48 h. and then diluted with water and extracted with ethyl acetate. The organic layer was dried over sodium sulfate and concentrated in rotary evaporator. The residue was purified using HPLC over a gradient of acetonitrile and water containing 0.1% trifluoroacetic acid to yield the desired compound (0.012 g, 65%). MS (ES) 334.1 (M+H)$^+$.

Example 2

Preparation of [3-Fluoro-2-(2-fluoro-phenyl)-quinolin-4-yl]-pyridin-3-yl-amine

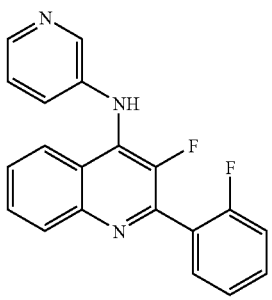

To a solution of 3-fluoro-2-(2-fluoro-phenyl)-4-iodo-quinoline (from Example 1, Step F, 0.02 g, 0.05 mmol) in dioxane (1 mL) was added cesium carbonate (0.05 g, 0.15 mmol) and Xanphos (0.0045 g, 0.001 mmol). The resulting mixture was degassed for 5 min and tris(dibenzylidineacetone)dipalladium(0) (0.0025 g, 0.0025 mmol) was added. The reaction mixture was stirred at 100° C. for 3 h, after which it was diluted with water and extracted with ethyl acetate. The organic layer was dried over sodium sulfate and concentrated in rotary evaporator. The residue was purified using HPLC over a gradient of acetonitrile and water containing 0.1% trifluoroacetic acid to yield the desired compound (0.012 g, 65%). MS (ES) 334.1 (M+H)$^+$.

Example 3

Preparation of (2-benzo[1,3]dioxol-5-yl-3-fluoro-quinolin-4-yl)-pyridin-4-yl-amine

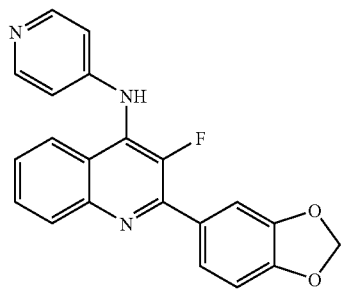

Step A. Preparation of 2-benzo[1,3]dioxol-5-yl-4-chloro-3-fluoro-quinoline

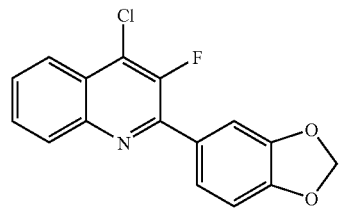

To a solution of 4-chloro-3-fluoro-2-iodo-quinoline (from Example 1, step D, 0.127 g, 0.41 mmol) in toluene (5 mL) was added n-butanol (2 mL), water (3 mL) and cesium carbonate (0.404 g, 1.2 mmol). The resulting mixture was degassed for 5 min., after which tetrakis(triphenylphosphine)palladium(0) (0.002 g, 5 mol %) and benzo[1,3]dioxole-5-boronic acid (0.086 g, 0.4 mmol) were added. The reaction mixture was stirred at 50° C. for 24 h. and then extracted with ethyl acetate. The organic layer was dried and concentrated in a rotary evaporator. The residue was purified by silica gel column chromatography using ethyl acetate/hexane gradient to yield the title compound (0.070 g, 57%). MS (ES) 302 (M+H)$^+$.

Step B: Preparation of
2-benzo[1,3]dioxol-5-yl-3-fluoro-4-iodo-quinoline

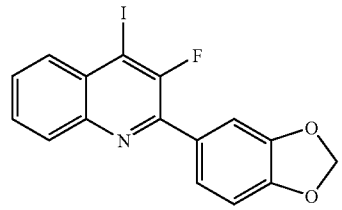

To a −78° C. solution of 2-benzo[1,3]dioxol-5-yl-4-chloro-3-fluoro-quinoline (from step A, 0.073 g, 0.24 mmol) in tetrahydrofuran (2 mL) was added butyl lithium (0.36 mL, 2.5 M in hexane, 0.6 mmol). The resulting reaction mixture was stirred for 3 h., after which a solution of iodine (0.06 g, 0.24 mmol) in 0.8 mL of THF was added. The reaction mixture was stirred for an additional 2 h. and diluted with water (20 mL). The aqueous layer was extracted with ethyl acetate (2×25 mL). The combined organic layers were dried over sodium sulfate, concentrated and purified via silica gel column chromatography to give the title compound (0.046 g, 48%). MS (ES) 393.8 (M+H)$^+$.

Step C. Preparation of (2-benzo[1,3]dioxol-5-yl-3-fluoro-quinoline-4-yl)-pyridin-4-yl-amine To a solution of 2-benzo[1,3]dioxol-5-yl-3-fluoro-4-iodo-quinoline (from Step B, 0.04 g, 0.1 mmol) in dioxane (1 mL) was added cesium carbonate (0.1 g, 0.3 mmol) and Xanphos (0.0045 g, 0.001 mmol). The mixture was degassed for 5 min., and then tris(dibenzylidineacetone)dipalladium(0) (0.0025 g, 0.0025 mmol) was added. The reaction mixture was stirred at 100° C. for 2 h., diluted with water and extracted with ethyl acetate. The organic layer was dried over sodium sulfate and concentrated in rotary evaporator. The residue was purified via HPLC over a reverse phase column using a gradient of acetonitrile and water containing 0.1% trifluoroacetic acid to yield the desired compound (0.009 g, 24%). MS (ES) 360.0 (M+H)$^+$.

Assay Methods

The following assay methods were used to evaluate the compounds of the present invention.

The autophosphorylation of GST-ALK5 was developed for primary screening of the compounds that inhibit TGF-β signaling by interacting with ALK5. HA-ALK5 assay is a secondary screening assay to confirm the inhibitory compounds that were selected from the primary screening, and also for the determination of IC$_{50}$ for each compound.

Autophosphorylation Assay of GST-ALK5

The cytoplasmic domain of ALK5 was fused to glutathione S-transferase (GST) and the GST-ALK5 fusion protein was expressed in a baculovirus expression system. GST-ALK5 was isolated with glutathione Sepharose 4B beads (Pharmacia Biotech, Sweden) and stored at −80° C. until use.

For detection of GST-ALK5 autophosphorylation and screening of inhibitory compounds, an aliquot of GST-ALK5 in 1× kinase buffer including [$^{33}$P]-γ-ATP was added to 96-well plates in the presence or absence of compounds. The mixture was then incubated at room temperature for 30 min and transferred to each well of a Filterplate with vacuum. The Filterplate was then washed 3 times and radioactivity in each well was counted in a Packard TopCount.

In Vitro Kinase of HA-ALK5

An expression construct containing full-length ALK5 C-terminally tagged with HA was transfected into COS7 cells, and HA-ALK5 was isolated by immunoprecipitation with anti-HA antibodies. Aliquots of immunoprecipitated HA-ALK5 in 1× kinase buffer plus [$^{33}$P]-γ-ATP was added to 96-well plates in the presence or absence of different concentrations of testing compounds, and incubated at room temperature for 60 min. The reaction mixture was then transferred to a Filterplate. The plate was washed three times and radioactivity in each well counted. IC$_{50}$ for each compound was determined using the Prism3 program.

ELISA Assay for TGF-β Stimulated Smad2 Phosphorylation

Serum-starved normal human lung fibroblasts (NHLF) in 24-well plate were treated with or without different concentrations of testing compounds for 30 min. The cells were then stimulated with TGF-β for one hour. After fixing, permeabilizing, and blocking, the cells were incubated with phospho-Smad2 specific antibodies followed by HRP-conjugated secondary antibody. The extent of Smad2 phosphorylation was then detected using HRP substrate and read with an ELISA plate reader. IC$_{50}$ for each testing compound was determined using the PRISM3 program.

ELISA Assay for TGF-β Stimulated PAI-1 Secretion

Serum-starved NHLF in 24-well plates were treated with or without different concentrations of testing compounds for 30 min. The cells were then stimulated with TGF-β and incubated in a 37° C. incubator for 24 hours. The media were collected and added to 96-well plates coated with anti-PAI-1 antibodies. The secreted PAI-1 was then detected with another PAI-1 specific antibody followed by HRP-conjugated secondary antibody. The secretion of PAI-1 was detected using HRP substrate and read with an ELISA plate reader. IC$_{50}$ for each testing compound was determined using the PRISM3 program.

SIRCOL Collagen Assay for TGF-β Stimulated Cells

Serum-starved NHLF in 24-well plates were treated with or without different concentrations of testing compounds for 30 min. The cells were then stimulated with TGF-β and incubated for 24 hours. The media were collected and SIRCOL dye reagent was added. After spinning and washing, the pellets were resuspended in alkali reagent and read with an ELISA plate reader. IC$_{50}$ for each testing compound was determined using the PRISM3 program.

Detection of TGF-β Stimulated Fibronectin Expression

Serum-starved NHLF in 24-well plates were treated with or without different concentrations of testing compounds for 30 min. The cells were then stimulated with TGF-β and incubated for 24 hours. After washing and fixing, the secreted fibronectin was incubated with fibronectin specific antibodies, followed by incubation with biotin-labeled secondary antibody, streptavidin-peroxidase and HRP substrate. The signal was then detected using an ELISA reader. IC$_{50}$ for each testing compound was determined using the PRISM3 program.

RESULTS

Some of the representative compounds having IC$_{50}$ value of <10 μM for TGF-β (ALK5) phosphorylation and in cell-based assays include compound Nos. 7, 51, 55, and 62-66 in Table 1. In addition, these compounds exhibited >50-100-fold selectivity for ALK5 (TGF-β) vs. closely related ALK6 and p38 kinases.

P-Smad2, PAI-1, collagen and fibronectin assays are cell-based assays that are used for determination of functional activities of the compounds from the secondary screening. Since all of the molecules are targets of TGF-β signaling, the data demonstrated that the compounds specifically inhibit TGF-β mediated signal transduction.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A method of treating a TGF-β stimulated proliferative disorder, in a patient in need thereof, comprising administering to said patient a compound of the formula:

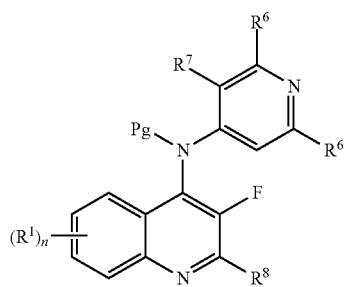

or a pharmaceutically acceptable salt thereof,
wherein
Pg is hydrogen, alkyl, or a nitrogen protecting group;
n is an integer from 0 to 3;
each $R^1$ substituent is independently selected from the group consisting of —$R^2$, -T-$R^2$, and —V-T-$R^2$;
each $R^2$ is independently selected from the group consisting of $C_{1-3}$ aliphatic, hydroxy, —$N(R^3)_2$, halo, cyano, —$OR^4$, —$C(O)R^4$, —$CO_2R^4$, —$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, phenyl which is optionally substituted with 1-3 $R^5$, 5-6 membered heterocyclyl which is optionally substituted with 1-3 $R^5$, and 5-6 membered heteroaryl which is optionally substituted with 1-3 $R^5$;
each T is independently $C_{1-5}$ alkylidene that is optionally interrupted by —O—, —C(O)—, —S—, —S(O)—, —$S(O)_2$—, or —$N(R^3)$—;
each V is independently selected from the group consisting of —O—, —S—, —S(O)—, —$S(O)_2$—, —C(O)—, —$N(R^3)$—, —$N(R^3)C(O)$—, or —$N(R^3)C(O)_2$—, —$N(R^3)S(O)_2$—, —$C(O)N(R^3)$—, —$S(O)_2N(R^3)$—, —$N(R^3)C(O)N(R^3)$—, and —OC(O)—;
each $R^3$ is independently selected from the group consisting of hydrogen, $C_{1-6}$ aliphatic, —$C(O)R^4$, —$C(O)_2R^4$, and —$SO_2R^4$,
or two $R^3$ on the same nitrogen together with their intervening nitrogen form a 5-6 membered heterocyclyl or heteroaryl ring having 1-3 ring heteroatoms selected from nitrogen, oxygen or sulfur;
each $R^4$ is independently selected from the group consisting of $C_{1-6}$ aliphatic, phenyl or a 5-6 membered heteroaryl or heterocyclyl having 1-3 ring heteroatoms selected from nitrogen, oxygen or sulfur;
$R^8$ is selected from the group consisting of:
(a) aryl, heteroaryl, and cycloalkyl, each of which is optionally substituted with 1-3 $R^5$, and
(b) alkyl;
each $R^5$ is independently selected from the group consisting of $C_{1-6}$ aliphatic, halo, —OH, —$N(R^3)_2$, cyano, —$C(O)R^4$, —$CO_2R^4$, —$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, —$OC(O)N(R^3)_2$, phenyl, 5-6 membered heterocyclyl and 5-6 membered heteroaryl,
or two adjacent $R^5$ on an aryl, cycloalkyl, or heteroaryl ring are taken together with their intervening atoms to form a 5-6 membered fused ring having 0-2 heteroatoms selected from nitrogen, oxygen or sulfur;
each $R^6$ is independently selected from the group consisting of hydrogen, halo, $C_{1-4}$ alkyl, $C_{1-4}$ alkoxy, $C_{1-4}$ monoalkylamino and $C_{1-4}$ dialkylamino; and
$R^7$ is selected from the group consisting of hydrogen, halo, —OH, —$N(R^3)_2$, cyano, —$OR^4$, —$C(O)R^4$, —$CO_2R^4$, —$SR^4$, —$S(O)R^4$, —$S(O)_2R^4$, —$N(R)^3C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, and —$OC(O)R^4$.

2. The method according to claim 1, wherein the disorder is selected from the group consisting of tumor growth and cancer.

3. The method according to claim 1, wherein the disorder is a fibroproliferative disease selected from the group consisting of: diabetic nephropathy, and idiopathic pulmonary fibrosis.

4. A method for inhibiting TGF-β activity in a subject, said method comprising administering to said subject a compound of the formula:

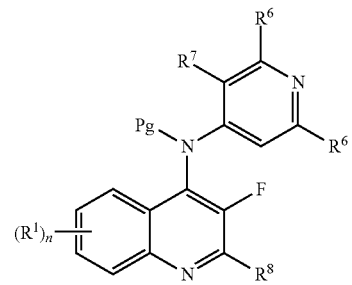

or a pharmaceutically acceptable salt or a prodrug thereof,
wherein
Pg is hydrogen, alkyl or a nitrogen protecting group;
n is an integer from 0 to 3;
each R1 substituent is independently selected from the group consisting of —$R^2$, -T-$R^2$, and —V-T-$R^2$;
each $R^2$ is independently selected from the group consisting of $C_{1-3}$ aliphatic, hydroxy, —$N(R^3)_2$, halo, cyano, —$OR^4$, —$C(O)R^4$, —$CO_2R^4$, —$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, phenyl which is optionally substituted with 1-3 $R^5$, 5-6 membered heterocyclyl which is optionally substituted with 1-3 $R^5$, and 5-6 membered heteroaryl which is optionally substituted with 1-3 $R^5$;
each T is independently $C_{1-5}$ alkylidene that is optionally interrupted by —O—, —C(O)—, —S—, —S(O)—, —$S(O)_2$—, or —$N(R^3)$—;
each V is independently selected from the group consisting of —O—, —S—, —S(O)—, —$S(O)_2$—, —C(O)—, —$N(R^3)$—, —$N(R^3)C(O)$—, or —$N(R^3)C(O)_2$—, —$N(R^3)S(O)_2$—, —$C(O)N(R^3)$—, —$S(O)_2N(R^3)$—, —$N(R^3)C(O)N(R^3)$—, and —OC(O)—;
each $R^3$ is independently selected from the group consisting of hydrogen, $C_{1-6}$ aliphatic, —$C(O)R^4$, —$C(O)_2R^4$, and —$SO_2R^4$,
or two $R^3$ on the same nitrogen together with their intervening nitrogen form a 5-6 membered heterocyclyl or heteroaryl ring having 1-3 ring heteroatoms selected from nitrogen, oxygen or sulfur;

each R⁴ is independently selected from the group consisting of C₁₋₆ aliphatic, phenyl or a 5-6 membered heteroaryl or heterocyclyl having 1-3 ring heteroatoms selected from nitrogen, oxygen or sulfur;

R⁸ is selected from the group consisting of:
(a) aryl, heteroaryl, and cycloalkyl, each of which is optionally substituted with 1-3 R⁵, and
(b) alkyl;

each R⁵ is independently selected from the group consisting of C₁₋₆ aliphatic, halo, —OH, —N(R³)₂, cyano, —OR⁴, —C(O)R⁴, —CO₂R⁴, —SR⁴, —S(O)R⁴, —S(O)₂R⁴, —N(R³)C(O)R⁴, —N(R³)CO₂R⁴, —N(R³)SO₂R⁴, —C(O)N(R³)₂, —SO₂N(R³)₂, —N(R³)C(O)N(R³)₂, —OC(O)R⁴, —OC(O)N(R³)₂, phenyl, 5-6 membered heterocyclyl and 5-6 membered heteroaryl, or two adjacent R⁵ on an aryl, cycloalkyl, or heteroaryl ring are taken together with their intervening atoms to form a 5-6 membered fused ring having 0-2 heteroatoms selected from nitrogen, oxygen or sulfur;

each R⁶ is independently selected from the group consisting of hydrogen, halo, C₁₋₄ alkyl, C₁₋₄ alkoxy, C₁₋₄ monoalkylamino and C₁₋₄ dialkylamino; and R⁷ is selected from the group of hydrogen, halo, —OH, —N(R³)₂, cyano, —C(O)R⁴, —CO₂R⁴, —SR⁴, —S(O)R⁴, —S(O)₂R⁴, —N(R³)C(O)R⁴, —N(R³)CO₂R⁴, —N(R³)SO₂R⁴, —C(O)N(R³)₂, —SO₂N(R³)₂, —N(R³)C(O)N(R³)₂, and —OC(O)R⁴.

5. The method according to claim 2, wherein the cancer is breast cancer.

6. The method according to claim 1, wherein Pg is hydrogen.

7. The method according to claim 6, wherein R⁸ is selected from the group consisting of phenyl, naphthyl, pyridyl, thienyl, furyl, each of which is optionally substituted with 1-3 R⁵, cyclohexyl, cyclopentyl, cyclopropyl, and t-butyl.

8. The method according to claim 7, wherein R⁸ is selected from the group consisting of 2-fluorophenyl, benzo[1,3]dioxol-5-yl, 2-trifluoromethylphenyl, 2-chlorophenyl, pyridin-4-yl, 2-methylphenyl, 2-methoxyphenyl, 3-fluorophenyl, 3-chlorophenyl, 5-chloro-thiophen-2-yl, 5-chloro-furan-2-yl, 5-methyl-thiophen-2-yl, 5-methyl-furan-2-yl, 4-methyl-thiophen-2-yl, 2,3-dihydro-benzofuran-5-yl, 2-methylsulfanylphenyl, 4-fluorophenyl, 2-methanesulfinylphenyl, 4-methoxyphenyl, 2-cyanophenyl, 2-amidophenyl, 4-hydroxyphenyl, 3-aminophenyl, 3-methoxyphenyl, 4-cyanophenyl, 2,6-dichlorophenyl, phenyl, 4-chlorophenyl, cyclohexyl, cyclopropyl, cyclopentyl, 4-methylsulfanylphenyl, t-butyl, 4-amidophenyl, naphthalen-2-yl, 4-methanesulfinylphenyl, and 2-bromophenyl.

9. The method according to claim 8, wherein R⁶ is hydrogen.

10. The method according to claim 9, wherein R⁷ is hydrogen.

11. The method according to claim 10, wherein each R¹ is independently selected from the group consisting of:
(a) thienyl which is optionally substituted with 1-3 R⁵;
(b) furyl which is optionally substituted with 1-3 R⁵;
(c) pyrrolyl which is optionally substituted with 1-3 R⁵;
(d) phenyl which is optionally substituted with 1-3 R⁵;
(e) halo,
(f) —OR⁴,
(g) —N(R³)₂; and
(h) —N(R³)-T—OR⁴.

12. The method according to claim 11 wherein said compound has the formula:

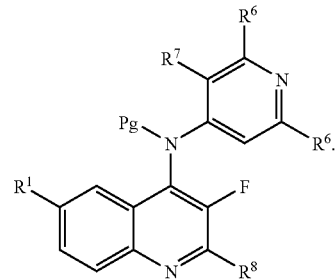

13. The method according to claim 12, wherein R¹ is selected from the group consisting of furyl, pyrrolyl, thienyl, phenyl which is optionally substituted with R⁵, and —N(R³)-T-OR⁴.

14. The method according to claim 11 wherein said compound has the formula:

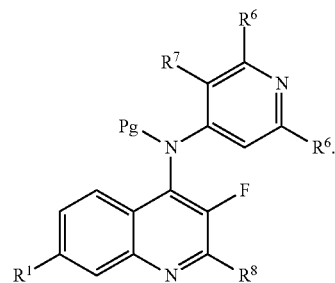

15. The method according to claim 14, wherein R¹ is selected from the group consisting of halo, —OR⁴, —N(R³)₂, and —N(R³)-T-OR⁴.

16. The method according to claim 1, wherein R⁸ is selected from the group consisting of phenyl, naphthyl, pyridyl, thienyl, furyl, each of which is optionally substituted with 1-3 R⁵, cyclohexyl, cyclopentyl, cyclopropyl, and t-butyl.

17. The method according to claim 16 wherein said compound has the formula:

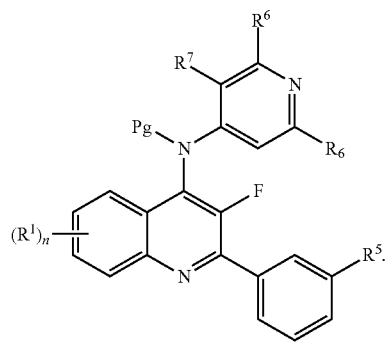

18. The method according to claim 16, wherein Pg, R⁶ and R⁷ are hydrogen.

19. The method according to claim 18, wherein each $R^1$ is independently selected from the group consisting of:
(a) thienyl which is optionally substituted with 1-3 $R^5$;
(b) furyl which is optionally substituted with 1-3 $R^5$;
(c) pyrrolyl which is optionally substituted with 1-3 $R^5$;
(d) phenyl which is optionally substituted with 1-3 $R^5$;
(e) halo,
(f) —$OR^4$,
(g) —$N(R^3)_2$; and
(h) —$N(R^3)$-T-$OR^4$.

20. The method according to claim 19, wherein n is 1.

21. The method according to claim 1 wherein said compound has the formula:

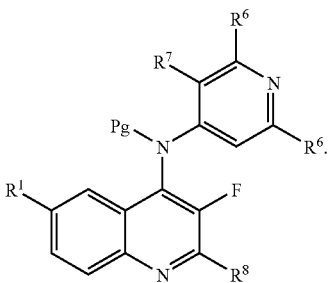

22. The method according to claim 1 wherein said compound has the formula:

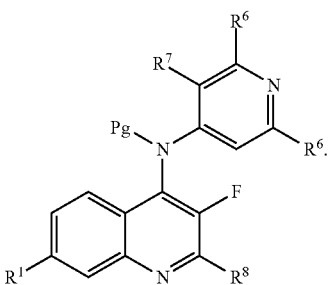

23. The method according to claim 1, wherein said compound is selected from the group consisting of:
[3-Fluoro-2-(2-methylsulfanyl-phenyl)-quinolin-4-yl]-pyridin-4-yl-amine,
[3-Fluoro-2-(2-methanesulfinyl-phenyl)-quinolin-4-yl]-pyridin-4-yl-amine,
2-[3-Fluoro-4-(pyridin-4-ylamino)-quinolin-2-yl]-benzonitrile,
2-[3-Fluoro-4-(pyridin-4-ylamino)-quinolin-2-yl]-benzamide,
[3-Fluoro-2-(4-fluoro-phenyl)-quinolin-4-yl]-pyridin-4-yl-amine,
[3-Fluoro-2-(4-methoxy-phenyl)-quinolin-4-yl]-pyridin-4-yl-amine,
[2-(3-Chloro-phenyl)-3-fluoro-quinolin-4-yl]-pyridin-4-yl-amine,
[3-Fluoro-2-(3-fluoro-phenyl)-quinolin-4-yl]-pyridin-4-yl-amine,
4-[3-Fluoro-4-(pyridin-4-ylamino)-quinolin-2-yl]-phenol,
[3-Fluoro-2-(3-methoxy-phenyl)-quinolin-4-yl]-pyridin-4-yl-amine,
[2-(2,6-Dichloro-phenyl)-3-fluoro-quinolin-4-yl]-pyridin-4-yl-amine,
[2-(4-Chloro-phenyl)-3-fluoro-quinolin-4-yl]-pyridin-4-yl-amine,
[2-(3-Amino-phenyl)-3-fluoro-quinolin-4-yl]-pyridin-4-yl-amine,
4-[3-Fluoro-4-(pyridin-4-ylamino)-quinolin-2-yl]-benzonitrile,
(3-Fluoro-2-phenyl-quinolin-4-yl)-pyridin-4-yl-amine,
(2-Cyclohexyl-3-fluoro-quinolin-4-yl)-pyridin-4-yl-amine,
(2-Cyclopropyl-3-fluoro-quinolin-4-yl)-pyridin-4-yl-amine,
(2-tert-Butyl-3-fluoro-quinolin-4-yl)-pyridin-4-yl-amine,
(3-Fluoro-2-naphthalen-2-yl-quinolin-4-yl)-pyridin-4-yl-amine,
(2-Cyclopentyl-3-fluoro-quinolin-4-yl)-pyridin-4-yl-amine,
[3-Fluoro-2-(4-methylsulfanyl-phenyl)-quinolin-4-yl]-pyridin-4-yl-amine,
4-[3-Fluoro-4-(pyridin-4-ylamino)-quinolin-2-yl]-benzamide,
(3-Fluoro-2-phenyl-quinolin-4-yl)-pyridin-4-yl-amine,
[3-Fluoro-2-(4-methanesulfinyl-phenyl)-quinolin-4-yl]-pyridin-4-yl-amine,
[3-Fluoro-2-(2-fluoro-phenyl)-quinolin-4-yl]-pyridin-4-yl-amine,
(2-Benzo[1,3]dioxol-5-yl-3-fluoro-quinolin-4-yl)-pyridin-4-yl-amine,
(3-Fluoro-2-pyridin-4-yl-quinolin-4-yl)-pyridin-4-yl-amine,
(3-Fluoro-2-o-tolyl-quinolin-4-yl)-pyridin-4-yl-amine,
[2-(2-Bromo-phenyl)-3-fluoro-quinolin-4-yl]-pyridin-4-yl-amine,
[3-Fluoro-2-(2-trifluoromethyl-phenyl)-quinolin-4-yl]-pyridin-4-yl-amine,
[2-(2-Chloro-phenyl)-3-fluoro-quinolin-4-yl]-pyridin-4-yl-amine,
[3-Fluoro-2-(2-methoxy-phenyl)-quinolin-4-yl]-pyridin-4-yl-amine,
3-Fluoro-2-(2-fluoro-phenyl)-N6-methyl-N4-pyridin-4-yl-quinoline-4,6-diamine,
3-Fluoro-2-(2-fluoro-phenyl)-N6-(2-methoxy-ethyl)-N4-pyridin-4-yl-quinoline-4,6-diamine,
[3-Fluoro-2-(2-fluoro-phenyl)-6-thiophen-3-yl-quinolin-4-yl]-pyridin-4-yl-amine,
2-Benzo[1,3]dioxol-5-yl-3-fluoro-N6-methyl-N4-pyridin-4-yl-quinoline-4,6-diamine,
2-Benzo[1,3]dioxol-5-yl-3-fluoro-N6-(2-methoxy-ethyl)-N4-pyridin-4-yl-quinoline-4,6-diamine,
[3-Fluoro-2-(2-fluoro-phenyl)-6-furan-2-yl-quinolin-4-yl]-pyridin-4-yl-amine,
(2-Benzo[1,3]dioxol-5-yl-7-bromo-3-fluoro-quinolin-4-yl)-pyridin-4-yl-amine,
2-Benzo[1,3]dioxol-5-yl-3-fluoro-N7-methyl-N4-pyridin-4-yl-quinoline-4,7-diamine,
2-Benzo[1,3]dioxol-5-yl-3-fluoro-N7-(2-methoxy-ethyl)-N4-pyridin-4-yl-quinoline-4,7-diamine,
(2-Benzo[1,3]dioxol-5-yl-3-fluoro-7-methoxy-quinolin-4-yl)-pyridin-4-yl-amine,
[3-Fluoro-2-(2-fluoro-phenyl)-7-methoxy-quinolin-4-yl]-pyridin-4-yl-amine, 3-Fluoro-2-(2-fluoro-phenyl)-N7-methyl-N4-pyridin-4-yl-quinoline-4,7-diamine,
[2-(3-Bromo-phenyl)-3-fluoro-quinolin-4-yl]-pyridin-4-yl-amine,
(2-Chloro-pyridin-4-yl)-[3-fluoro-2-(5-methyl-furan-2-yl)-quinolin-4-yl]-amine,
(2-Chloro-pyridin-4-yl)-[2-(5-chloro-thiophen-2-yl)-3-fluoro-quinolin-4-yl]-amine,
(2-Chloro-pyridin-4-yl)-[3-fluoro-2-(3-fluoro-phenyl)-quinolin-4-yl]-amine,
[3-Fluoro-2-(5-methyl-furan-2-yl)-quinolin-4-yl]-methyl-pyridin-4-yl-amine, and
(2-Chloro-pyridin-4-yl)-[2-(5-chloro-thiophen-2-yl)-3-fluoro-quinolin-4-yl]-methyl-amine.

* * * * *